United States Patent
el Kaliouby et al.

(10) Patent No.: US 10,799,168 B2
(45) Date of Patent: Oct. 13, 2020

(54) INDIVIDUAL DATA SHARING ACROSS A SOCIAL NETWORK

(71) Applicant: Affectiva, Inc., Boston, MA (US)

(72) Inventors: Rana el Kaliouby, Milton, MA (US); Richard Scott Sadowsky, Sturbridge, MA (US); Oliver Orion Wilder-Smith, Holliston, MA (US)

(73) Assignee: Affectiva, Inc., Boston, MA (US)

( * ) Notice: Subject to any disclaimer, the term of this patent is extended or adjusted under 35 U.S.C. 154(b) by 0 days.

(21) Appl. No.: 15/720,301

(22) Filed: Sep. 29, 2017

(65) Prior Publication Data

US 2018/0035938 A1    Feb. 8, 2018

Related U.S. Application Data

(63) Continuation-in-part of application No. 13/297,342, filed on Nov. 16, 2011, now abandoned, and a
(Continued)

(51) Int. Cl.
*A61B 5/16* (2006.01)
*G06K 9/62* (2006.01)
(Continued)

(52) U.S. Cl.
CPC ............ *A61B 5/165* (2013.01); *G06K 9/6201* (2013.01); *G06Q 10/101* (2013.01); *G06Q 50/01* (2013.01);
(Continued)

(58) Field of Classification Search
CPC .......... G06K 9/00275; G06K 9/00281; G06K 9/0028; G06K 9/00295; G06K 9/00302;
(Continued)

(56) References Cited

U.S. PATENT DOCUMENTS 3,034,500 A    5/1962   Backster, Jr.
3,548,806 A    12/1970  Fisher
(Continued)

FOREIGN PATENT DOCUMENTS

JP          08115367       7/1996
KR    10-2005-0021759 A    3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley J Tucker
(74) *Attorney, Agent, or Firm* — Adams Intellex, PLC

(57) ABSTRACT

Facial image data of an individual is collected of the individual to provide mental state data using a first web-enabled computing device. The mental state data is analyzed to produce mental state information using a second web-enabled computing device. The mental state information is shared across a social network using a third web-enabled computing device. The mental state data is also collected from the individual through capture of sensor information. The mental state data is also collected from the individual through capture of audio data. The individual elects to share the mental state information across the social network. The mental state data may be collected over a period of time and analyzed to determine a mood of the individual. The mental state information is translated into a representative icon for sharing, which may include an emoji. An image of the individual is shared along with the mental state information.

29 Claims, 25 Drawing Sheets

Related U.S. Application Data continuation-in-part of application No. 15/395,750, filed on Dec. 30, 2016, which is a continuation-in-part of application No. 15/262,197, filed on Sep. 12, 2016, now abandoned, which is a continuation-in-part of application No. 14/796,419, filed on Jul. 10, 2015, now abandoned, which is a continuation-in-part of application No. 13/153,745, filed on Jun. 6, 2011, now abandoned, said application No. 14/796,419 is a continuation-in-part of application No. 14/460,915, filed on Aug. 15, 2014, which is a continuation-in-part of application No. 13/153,745, filed on Jun. 6, 2011, now abandoned.

(60) Provisional application No. 62/439,928, filed on Dec. 29, 2016, provisional application No. 62/442,325, filed on Jan. 4, 2017, provisional application No. 62/448,448, filed on Jan. 20, 2017, provisional application No. 62/442,291, filed on Jan. 4, 2017, provisional application No. 62/469,591, filed on Mar. 10, 2017, provisional application No. 62/503,485, filed on May 9, 2017, provisional application No. 62/524,606, filed on Jun. 25, 2017, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/549,560, filed on Oct. 20, 2011, provisional application No. 62/273,896, filed on Dec. 31, 2015, provisional application No. 62/301,558, filed on Feb. 29, 2016, provisional application No. 62/370,421, filed on Aug. 3, 2016, provisional application No. 62/217,872, filed on Sep. 12, 2015, provisional application No. 62/222,518, filed on Sep. 23, 2015, provisional application No. 62/265,937, filed on Dec. 10, 2015, provisional application No. 62/273,896, filed on Dec. 31, 2015, provisional application No. 62/301,558, filed on Feb. 29, 2016, provisional application No. 62/370,421, filed on Aug. 3, 2016, provisional application No. 62/023,800, filed on Jul. 11, 2014, provisional application No. 62/047,508, filed on Sep. 8, 2014, provisional application No. 62/082,579, filed on Nov. 20, 2014, provisional application No. 62/128,974, filed on Mar. 5, 2015, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014, provisional application No. 62/023,800, filed on Jul. 11, 2014, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011.

(51) Int. Cl.

| | | |
|---|---|---|
| H04L 29/08 | (2006.01) | |
| G06Q 50/00 | (2012.01) | |
| G06Q 10/10 | (2012.01) | |
| G16H 40/67 | (2018.01) | |
| G16H 50/20 | (2018.01) | |
| G16H 40/63 | (2018.01) | |

(52) U.S. Cl.
CPC ............ *G16H 40/63* (2018.01); *G16H 40/67* (2018.01); *G16H 50/20* (2018.01); *H04L 67/306* (2013.01)

(58) Field of Classification Search
CPC .......... G06K 9/00308; G06K 9/00315; G06K 9/00335; G06K 9/00342; G06K 9/00348; G06K 9/00355; G06K 9/00362; G06K 9/00241
See application file for complete search history.

(56) References Cited

U.S. PATENT DOCUMENTS

| | | | |
|---|---|---|---|
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A | 11/1996 | Wildes et al. | |
| 5,619,571 A | 4/1997 | Sandstorm et al. | |
| 5,647,834 A * | 7/1997 | Ron ........................ | A61B 5/16 600/23 |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,508 A | 6/1998 | Sugita et al. | |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,091,334 A | 7/2000 | Galiana et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |

(56) References Cited

U.S. PATENT DOCUMENTS

| | | |
|---|---|---|
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 * | 10/2006 | Dryer .................... G06Q 30/02 715/863 |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 7,921,369 B2 | 4/2011 | Bill |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 9,020,185 B2 | 4/2015 | Mestha |
| 10,268,640 B1 * | 4/2019 | Harte .................. G06F 16/24575 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0182123 A1 | 9/2003 | Mitsuyoshi |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 * | 8/2005 | Matsugu .................. A61B 5/16 600/301 |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0170945 A1 * | 8/2006 | Bill ........................ H04L 29/06 358/1.13 |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 * | 11/2008 | Kurtz ...................... A61B 3/10 382/128 |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0128567 A1 | 5/2009 | Shuster et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0193344 A1 | 7/2009 | Smyers |
| 2009/0203998 A1 | 8/2009 | Klinghul |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0285456 A1 | 11/2009 | Moon et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0198757 A1 | 8/2010 | Cheng et al. |
| 2010/0223341 A1 | 9/2010 | Manolescu |
| 2010/0223581 A1 * | 9/2010 | Manolescu ............ G06Q 10/00 715/853 |
| 2010/0240416 A1 | 9/2010 | Knight |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 * | 6/2011 | Holopainen ........ G06K 9/00308 455/414.1 |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2011/0294525 A1 * | 12/2011 | Jonsson .................. G06F 17/27 455/466 |
| 2011/0301433 A1 | 12/2011 | Sadowsky et al. |
| 2012/0311032 A1 | 12/2012 | Murphy et al. |
| 2012/0324491 A1 | 12/2012 | Bathiche et al. |
| 2013/0019187 A1 | 1/2013 | Hind et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2013/0290427 A1 | 10/2013 | Proud |
| 2014/0172910 A1 | 6/2014 | Jung et al. |

(56) References Cited

U.S. PATENT DOCUMENTS

| | | | |
|---|---|---|---|
| 2016/0104486 A1 | 4/2016 | Penilla et al. | |
| 2017/0003784 A1 | 1/2017 | Garg et al. | |
| 2017/0262695 A1* | 9/2017 | Ahmed | G06K 9/00288 |

FOREIGN PATENT DOCUMENTS

| | | | |
|---|---|---|---|
| KR | 10-2008-0016303 A | 2/2008 | |
| KR | 1020100048688 A | 5/2010 | |
| WO | WO 2011/045422 A1 | 4/2011 | |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1543.

Fasel, B. (Aug. 2002). Robust face analysis using convolutional neural networks. In Object recognition supported by user interaction for service robots (vol. 2, pp. 40-43). IEEE.

Matsugu, M., Mori, K., Mitari, Y., & Kaneda, Y. (2003). Subject independent facial expression recognition with robust face detection using a convolutional neural network. Neural Networks, 16(5-6), 555-559.

* cited by examiner

INDIVIDUAL DATA SHARING ACROSS A SOCIAL NETWORK

RELATED APPLICATIONS

This application claims the benefit of U.S. provisional patent applications "Image Analysis Framework using Remote Learning with Deployable Artifact" Ser. No. 62/439,928, filed Dec. 29, 2016, "Audio Analysis Learning using Video Data" Ser. No. 62/442,325, filed Jan. 4, 2017, "Vehicle Manipulation using Occupant Image Analysis" Ser. No. 62/448,448, filed Jan. 20, 2017, "Smart Toy Interaction using Image Analysis" Ser. No. 62/442,291, filed Jan. 4, 2017, "Image Analysis for Two-sided Data Hub" Ser. No. 62/469,591, filed Mar. 10, 2017, "Vehicle Artificial Intelligence Evaluation of Mental States" Ser. No. 62/503,485, filed May 9, 2017, and "Image Analysis for Emotional Metric Generation" Ser. No. 62/524,606, filed Jun. 25, 2017.

This application is also a continuation-in-part of "Sharing Affect Data Across a Social Network" Ser. No. 13/297,342, filed Nov. 16, 2011, which claims the benefit of U.S. provisional patent applications "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, and "Mental State Analysis of Voters" Ser. No. 61/549,560, filed Oct. 20, 2011.

This application is also a continuation-in-part of U.S. patent application "Image Analysis using Sub-sectional Component Evaluation to Augment Classifier Usage" Ser. No. 15/395,750, filed Dec. 30, 2016, which claims the benefit of U.S. provisional patent applications "Image Analysis Using Sub-Sectional Component Evaluation to Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Image Analysis using Sub-sectional Component Evaluation to Augment Classifier Usage" Ser. No. 15/395,750, filed Dec. 30, 2016, is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

Each of the foregoing applications is hereby incorporated by reference in its entirety.

FIELD OF INVENTION

This application relates generally to data sharing and more particularly to individual data sharing across a social network.

BACKGROUND

Many people desire to share data with the people in their lives. Applications that allow people to post individual data have grown in popularity and number in recent years and can occupy great amounts of time for many people. An individual posting data about herself, such as a picture from a recent vacation or the latest interesting lunch they ate, has become extremely common. Other postings that are commonplace today include product reviews, opinions, and blogs or news articles on particular topics, to name just a few.

People spend a tremendous amount of time on the internet, much of that includes the viewing and interacting with web pages including websites for social networks. The evaluation of mental states is key to understanding individuals and the way in which they react to the world around them. The world individuals react to more and more includes the virtual world. Mental states run a broad gamut from happiness to sadness, from contentedness to worry, from excitement to calmness, as well as numerous others. These mental states are experienced in response to everyday events in the real world such as frustration during a traffic jam, boredom while standing in line, impatience while waiting for a cup of coffee, and even in the virtual world as people interact with their computers and the internet. Individuals may become rather perceptive and empathetic based on evaluating and understanding others' mental states, but automated evaluation of mental states is far more challenging. An empathetic person may perceive someone being anxious or joyful and respond accordingly. The ability and means by which one person perceives another's emotional state may be quite difficult to summarize and has often been communicated as having a "gut feel."

Human emotions often result in facial expressions. The human face has over forty muscles, and these muscles act in coordination with each other to produce numerous facial expressions. The facial expressions can represent emotions such as anger, fear, sadness, disgust, contempt, surprise, and happiness. Facial muscles cause expressions by brow raising, smiling, nose wrinkling, and other actions that are all indicative of emotions or reactions to an external stimulus. For example, a person might wrinkle his nose in response to an unpleasant smell, smile in response to something he finds funny, and lower his brow in response to something invoking confusion or skepticism.

Different people may respond differently to a given stimulus. For example, some people may smile when afraid or nervous. Thus, there is a difference between a facial expression and a mental state. The smile a person produces when nervous may be different than the smile produced when the person is happy. Mental or emotional states can play a role in how people interpret external stimuli. Emotions such as happiness, sadness, fear, laughter, relief, angst, worry, anguish, anger, regret, and frustration are often reflected in facial expressions. Thus, the study of facial expressions and their meanings can provide important insight into human behavior.

SUMMARY

Analysis of an individual, as he interacts with the interne, various media, and with other people, may be performed by gathering mental state data via methods including the evaluation of facial expressions, head gestures, and physiological conditions. The mental state data may be analyzed to produce mental state information. Some of the mental state information resulting from the analysis may then be shared across a social network. A computer implemented method for data sharing is disclosed comprising: collecting mental state data of an individual on a first web-enabled computing device, wherein the mental state data includes facial image data of the individual; analyzing the mental state data, using a second web-enabled computing device, to produce mental state information; and sharing the mental state information, using a third web-enabled computing device, across a social network. The method may further comprise the individual electing to share their mental state information.

The method may further comprise presenting the mental state information to the individual, prior to the electing. The mental state data may be collected over a period of time, such that the mental state information that is shared is a reflection of an overarching mood for the individual. The mood may include one of a group comprising frustration, confusion, disappointment, hesitation, cognitive overload, focusing, being engaged, attending, boredom, exploration, confidence, trust, delight, and satisfaction. The sharing may include posting mental state information to a social network web page. The method may further comprise uploading the mental state information to a server. The method may further comprise distributing the mental state information across a computer network. The mental state data may include one of a group comprising physiological data, facial data, and actigraphy data. A web-enabled camera connected to a computing device may be used to capture one or more of the facial data and the physiological data. The facial data may include information on one or more of a group comprising facial expressions, action units, head gestures, smiles, brow furrows, squints, lowered eyebrows, raised eyebrows, and attention. The physiological data may include one or more of electrodermal activity, heart rate, heart rate variability, skin temperature, and respiration. The mental state data may be collected using a biosensor.

The method may further comprise inferring of mental states based on the mental state data which was collected. The method may further comprise identifying similar mental states within the social network. The mental states may include one of a group comprising frustration, confusion, disappointment, hesitation, cognitive overload, focusing, being engaged, attending, boredom, exploration, confidence, trust, delight, and satisfaction. The method may further comprise communicating an image of the individual with the mental state information that is being shared. The image of the individual may be from a peak time of mental state activity. The image may include a video. The method may further comprise restricting distribution of the mental state information to a specific subset of the social network. The method may further comprise sharing aggregated mental state information across the social network. The mental state data may be collected as the individual interacts with a web-enabled application. The web-enabled application may be one of a group comprising a landing page, a checkout page, a webpage, a website, a video on the web-enabled application, a game on the web-enabled application, a trailer, a movie, an advertisement, and a virtual world. The method may further comprise forwarding a reference to the web-enabled application as a part of the sharing of the mental state information. The reference may include a URL and a timestamp. The forwarding may include an image of material from the web-enabled application. The forwarding may include a video of material from the web-enabled application. The sharing may be part of a rating system for the web-enabled application. The sharing may include translating mental state information into a representative icon. The representative icon may comprise an emoji.

In some embodiments, a computer program product embodied in a non-transitory computer readable medium for data sharing is disclosed, the computer program product comprising code which causes one or more processors to perform operations of: collecting mental state data of an individual on a first web-enabled computing device, wherein the mental state data includes facial image data of the individual; analyzing the mental state data of the individual, using a second web-enabled computing device, to produce mental state information; electing, by the individual, to share the mental state information; and sharing the mental state information, using a third web-enabled computing device, across a social network. In some embodiments, a system for data sharing is disclosed: a memory for storing instructions; one or more processors attached to the memory wherein the one or more processors are configured to: collect mental state data of an individual on a first web-enabled computing device, wherein the mental state data includes facial image data of the individual; analyze the mental state data of the individual, using a second web-enabled computing device, to produce mental state information; receive an instruction, from the individual, to elect to share the mental state information; and share the mental state information, using a third web-enabled computing device, across a social network.

In some embodiments, a computer implemented method for data sharing is disclosed comprising: receiving mental state data of an individual on a first web-enabled computing device, wherein the mental state data includes facial image data of the individual; inferring mental states for the individual, using a second web-enabled computing device, based on the mental state data which was received; and sharing the mental states which were inferred, using a third web-enabled computing device, across a social network.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

Figure 1:
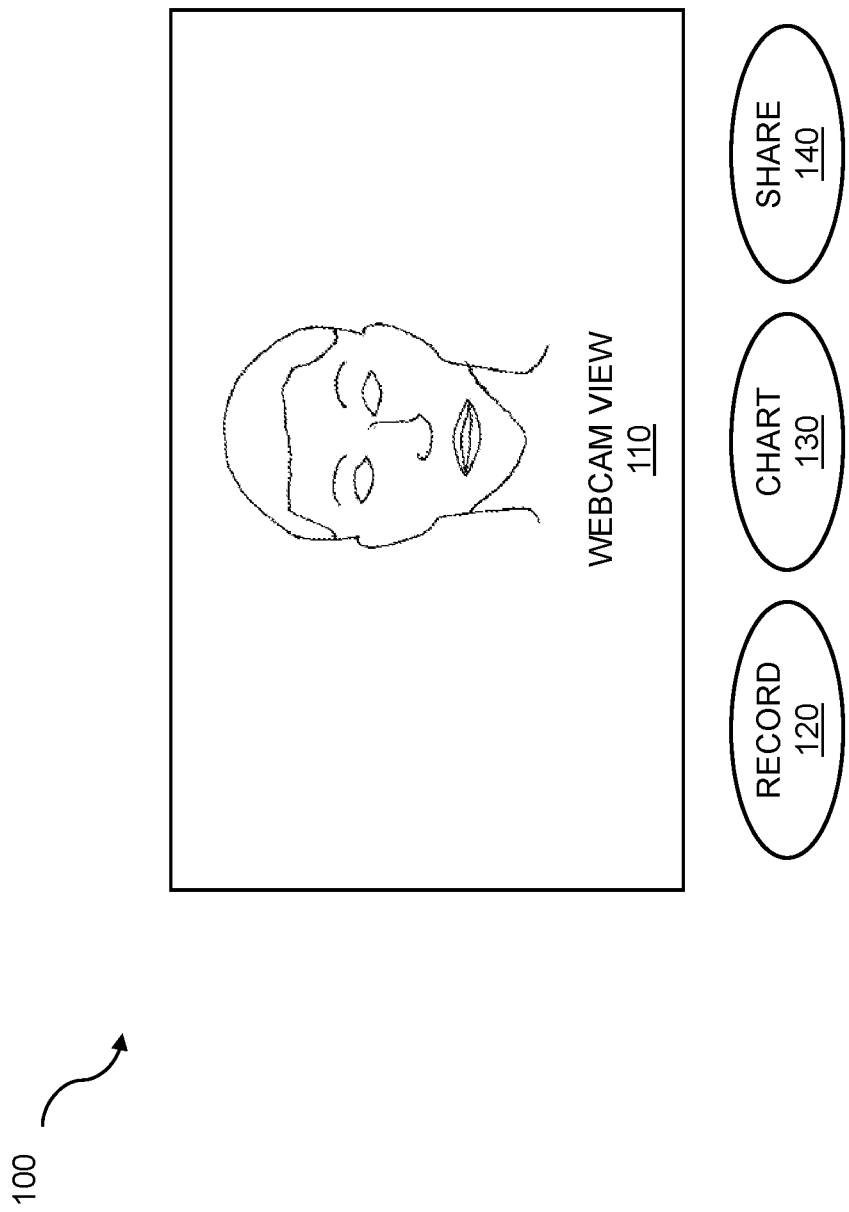
FIG. 1 is a diagram of a webcam view screen.

The present disclosure provides a description of various methods and systems for analyzing a person's mental states as she interacts with websites, web-enabled applications and/or other features on the internet, or other individuals, with the result being shared across a social network. Social networking has become more and more a part of everyday life, as our society is constantly connected through the Internet or other communication networks. Communication is accomplished by email, postings, texting, short messages, and the like, but communication of emotions has remained a challenge. Because an individual's emotions may be mysterious at times, and even misunderstood by the person themselves, performing mental state analysis and then communicating those mental states across a social network, virtual communication must become much more attuned to the individual. The communication is not limited to explicit postings and instead allows automatic communication of emotion. Such analysis and automatic communication of emotion is much different than a person merely posting their own perceived mental states. Mental states may include emotional states and/or cognitive states. Examples of emotional states include happiness or sadness. Examples of cognitive states include concentration or confusion. Observing, capturing, and analyzing these mental states can yield significant information about people's reactions that far exceed current capabilities in website type analytics and even an individual's own self-analysis and self-posting.

A challenge solved by this disclosure is the collection and analysis of mental states of an individual to produce mental state information that may be shared across a social network. Mental state data may be collected from an individual while performing specific tasks or over longer periods of time. Mental state data may include physiological data from sensors, facial data from a webcam connected to a computing device, or actigraphy data. The mental state data may be analyzed to create mental state information. The analysis may be performed on a different computing device than the mental state data capture. Mental state information may include moods, other mental states, mental state data or mental state information derived or inferred from mental state data. Mental states of the individual may include frustration, confusion, disappointment, hesitation, cognitive overload, focusing, being engaged, attending, boredom, exploration, confidence, trust, delight, and satisfaction or other emotions or cognitive states. Mental state information may relate to a specific stimulus, such as reacting to a web-enabled application, or may be a mood, which may relate to a longer period of time and may indicate, for example, a mental state for the day.

The individual may be given an opportunity to share their mental state with others. If the individual elects (opts-in) for sharing, their mental state may be shared over a social network. The sharing may be performed by a different computing device than the computing device of the collecting or analyzing. In embodiments, two or more of the computing devices are actually the same device. For example, a smartphone with an integrated webcam may collect mental state data in the form of facial data corresponding, at least in part, to an individual's mental state. The mental state data may then be sent over a network, such as the Internet, to a computing device comprising a server that is part of a cloud service for analysis. The resulting analysis may then provide mental state information, including mental states, corresponding to the mental state data back to the smartphone. The smartphone may then enable sending some or all of the mental state information, including translations of the mental state information into representative icons, across a social network. Thus two of the computing devices in this example are the same computing device. In embodiments, a first computing device performs the collecting, a second computing device performs the analyzing, and a third computing device performs the sharing. In embodiments, the first computing device and the second computing device are the same device. In other embodiments, the second computing device and the third computing device are the same device. In other embodiments, the first computing device and the third computing device are the same device. In further embodiments, the first computing device, the second computing device, and the third computing device are the same device.

The mental state may be shared over a social network by posting mood information on a social media or social network web page. The mental state shared may be an overall mood or may be a reaction to a specific stimulus. If the mental state is a reaction to a specific stimulus, a reference to the stimulus, such as a web-enabled application, may be shared. The reference may include a uniform reference locator (URL) and/or a timestamp. An image of the individual corresponding to their mood may be posted along with the mental state. Other individuals on the social network having a similar mental state may be identified to the individual. And in some cases the mental states of an individual's contacts on the social network may be aggregated and shared on the social network. In embodiments, a computer implemented method for data sharing comprising: collecting mental state data of an individual on a first web-enabled computing device, wherein the mental state data includes facial image data of the individual; analyzing the mental state data, using a second web-enabled computing device, to produce mental state information; and sharing the mental state information, using a third web-enabled computing device, across a social network.

FIG. 1 is a diagram of a webcam view screen. The webcam is integrated in or connected to a computing device for real-time or near-real-time processing or analysis of mental state data. A computing device executes code in the collecting of mental state data or the analyzing of mental state data or both. By contrast, a surveillance system may have a webcam connected to a display. By contrast, such a system may have a webcam connected to a storage device for later retrieval, but not for real-time or near-real-time analysis. By contrast, such a system may have a webcam connected to an electronic device that only provides only detection, for example, of whether a webcam image is changing. None of these contrasting examples is comprehended by the computing device of the current invention. A webcam view 110 of diagram 100 may include a view of an individual. The webcam view 110 may be obtained by a webcam or some other camera device attached to a computer or computing device. The view of the individual may show a video of the person's head, the whole person, or some portion of the person. A person's head may be viewed where the face is shown and facial expressions may be observed. The facial expressions may include facial actions and head gestures. Facial data may be observed including facial actions and head gestures used to infer mental states. Further, the observed data may include information on hand gestures or body language and body movements such as visible fidgets. In various embodiments these movements may be captured by cameras or by sensor readings. Facial data may include the tilting the head to the side, leaning forward, a smile, a frown, as well as many other gestures or expressions. The facial data may include information such as facial expressions, action units, head gestures, smiles, brow furrows, squints, lowered eyebrows, raised eyebrows, and attention. The webcam observations may include a blink rate for the eyes. For example, a reduced blink rate may indicate significant engagement in what is being observed. The webcam observations may also capture physiological information. Observations via the webcam may be accomplished while an individual is going through their normal tasks while using a computer. Observations may also be performed while specific items are being viewed, or interacted with, such as a web-enabled application, a video on a web-enabled application, a game on a web-enabled application, and a virtual world. In some embodiments, the webcam view 110 may become smaller, may become an icon, or may disappear, while the individual is interacting with a web-enabled application. In some embodiments, observations are performed while normal events of the day transpire.

A record button 120 may be included to record the webcam view 110. The record button 120 may be part of the "opting in" by the individual in the webcam view 110 where permission is obtained for observing mental state information and sharing this information. The record button 120 may be moused over to explain the purpose of the record button 120. The record button 120 may be clicked in order to start the recording. The record button may be clicked again to stop the recording. In some embodiments, recording may be accomplished based on sensing context. Recording can automatically begin as viewing or interaction begins with a specific web-enabled application. Recording can automatically end at a specific point in time or as a web-enabled application reaches its ending point. One such example is a series of video trailers that may be viewed. Recording of the webcam view can begin and end with the start and termination of each video trailer. In embodiments, permission may be granted for recording of the webcam view for certain contexts of operation. Further, the context may be recorded as well as the webcam view.

A chart button 130 may be used to display analytics of the information collected while the webcam was recording. The chart button 130 may be moused over to explain the purpose of the button. The chart button 130 may be clicked on to display a chart such as that shown in FIG. 2. The chart button 130 may be clicked before the sharing of the mental state information so that a person can determine whether he or she wants to share their mental state information with others. A share button 140 may be used for sharing the mental state information collected when the record button 120 is clicked. The share button 140 may be part of the "opting in" process of sharing mental state information with others. The share button 140 may be moused over to explain the purpose of the button. The share button 140 may be clicked to share mental state information with an individual, a group of people, or a social network. By clicking the share button 140 the mental state information may be communicated by email, may be posted to Facebook™, may be shared by Twitter™, or other social networking site. Sharing of mental state information may be a one-time occurrence or may be continuous. Once sharing is initiated, mental state information may be posted regularly to a social networking site. In this manner, a person's mental state information may be broadcast to their social network automatically and without the person's direct involvement. Sharing may also communicate a reference to a web-enabled application or the web-enabled application itself. The reference to the web-enabled application could be, for example, a web-page link. Based on this sharing the individual could communicate what they viewed and their mental states while viewing it. The individual could further request an elicited response from the individual or people with whom they are sharing their mental states.

Figure 2:
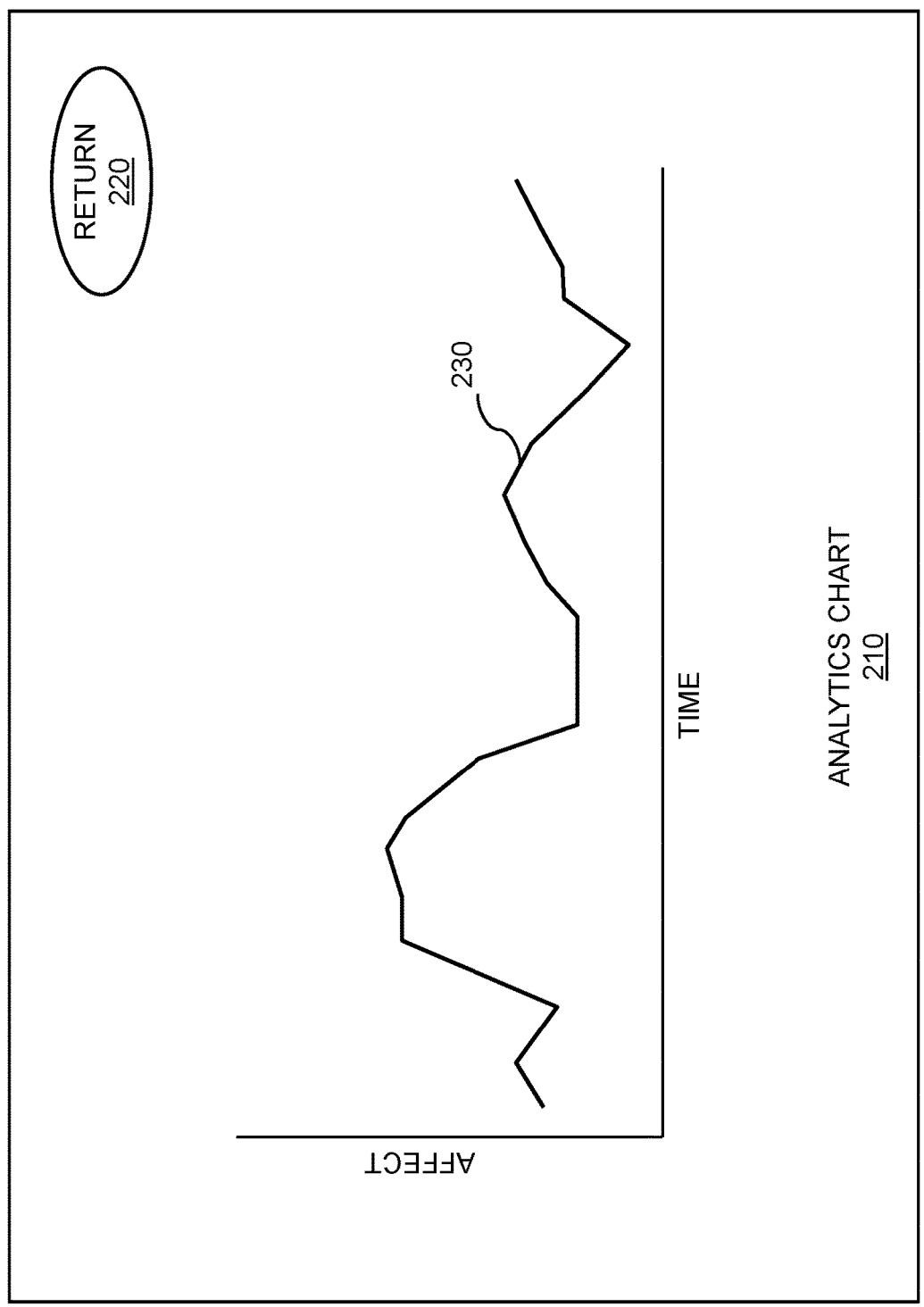
FIG. 2 is diagram of an analytics chart for affect data.

FIG. 2 is a diagram of an analytics chart 210 for affect data. The analytics chart 210 may include "time" on the x-axis and "affect" on the y-axis. A graph 230 may be shown that describes the affect data over time. The time period shown may be for a recent period of time when the individual was performing a variety of tasks, or for a specific task such as when the mental state data is collected as the individual interacts with a web-enabled application. The affect data may be as simple as a head gesture, such as indicating when an individual is leaning toward the screen. Leaning toward the screen can be an indicator of greater interest in what is being viewed on the screen. Affect data could also be an action unit used in mental state analysis. The action units may include the raising of an eyebrow, raising of both eyebrows, a twitch of a smile, a furrowing of the eye brows, flaring of nostrils, squinting of the eyes, and many other possibilities. These action units may be automatically detected by a computer system analyzing the video in real-time or near-real-time. Affect data could also be the evaluation of one or more mental states. For example, a graph could show positive or negative reactions. In some embodiments, a color could be used instead of a graph. For instance green could denote a positive reaction, while red could denote a negative reaction. Affect data could also be graphically displayed for a more specific mental state evaluation. For example, a single mental state could be graphed. Some of the mental states which could be graphed include frustration, confusion, disappointment, hesitation, cognitive overload, focusing, being engaged, attending, boredom, exploration, confidence, trust, delight, and satisfaction. In some embodiments, a smile track may be displayed which provides a line for each occurrence of a smile. As a smile is longer and more pronounced the line for the smile can be darker and more pronounced. Just as a chart button 130 can be selected from FIG. 1, a return button 220 can be selected from window 200 displayed in FIG. 2. The return button 220 may, in various embodiments, return the window to showing a webcam view, the previous web-enabled application, or the like.

Figure 3:
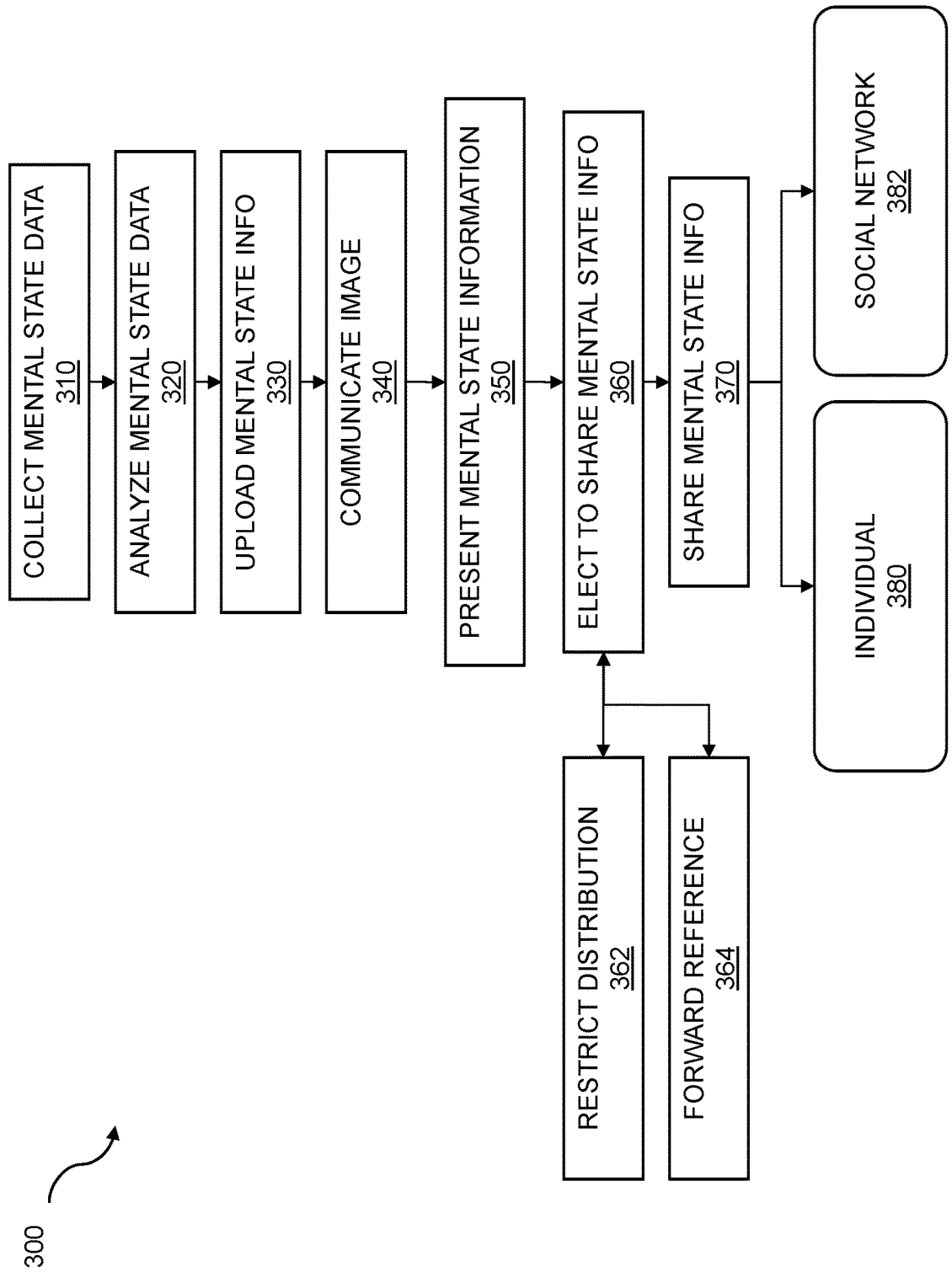
FIG. 3 is a flow diagram for sharing mental state information.

FIG. 3 is a flowchart for sharing mental state information. A flow 300 may begin with collecting mental state data 310 of an individual on a first web-enabled computing device, wherein the mental state data of the individual includes facial image data of the individual. The mental state data may include collecting action units, collecting facial expressions, and the like. Physiological data may be obtained from video observations of a person. For example heart rate, heart rate variability, autonomic activity, respiration, and perspiration may be observed from video capture. Alternatively, in some embodiments, a biosensor may be used to capture physiological information and may also be used to capture accelerometer readings. Permission may be requested and obtained prior to the collection of mental state data 310. The mental state data may be collected by a client computer system, by a tablet, by a smartphone, and so on.

In embodiments, the collecting mental state data of an individual includes collecting audio data. The audio data can be collected on the same computing device or a different computing device. The audio data can be collected using an integrated microphone of a smartphone, for example. The audio data can include spoken words of the individual. The audio data can be tied in a contemporaneous manner to facial image data of the individual. That is, the facial image data and the audio data can both be tied in time to the same mental state data. For example, raised eyebrows (facial) and an utterance of the expression "No way!" can happen at the same, or approximately the same, moment in time and thus relate to the same mental state data. However, audio data can also be collected such that spoken words of the individual are not contemporaneous with any corresponding facial data. For example, an individual may have spilled his coffee off camera and uttered one or more expletives not connected to any collected facial image data. Nonetheless, the mental state data from the non-contemporaneously collected audio data may be very valuable in subsequent mental state data analysis. Furthermore, the audio data may be related primarily to background sounds and noises and not include any spoken words of the individual. Therefore, in embodiments, the audio data includes contemporaneously spoken words of the individual, non-contemporaneously spoken words of the individual, or background audio data. In embodiments, analyzing the mental state data, using a second web-enabled computing device, to produce mental state information, wherein the analyzing the mental state data of the individual includes analyzing the audio data that was collected.

The flow 300 may continue with analyzing the mental state data 320 to produce mental state information. While mental state data may be raw data such as heart rate, mental state information may include information derived from the raw data. The mental state information may include the mental state data. The mental state information may include valence and arousal. The mental state information may include the mental states experienced by the individual. Some embodiments may include inferring of mental states based on the mental state data which was collected.

Figure 8:
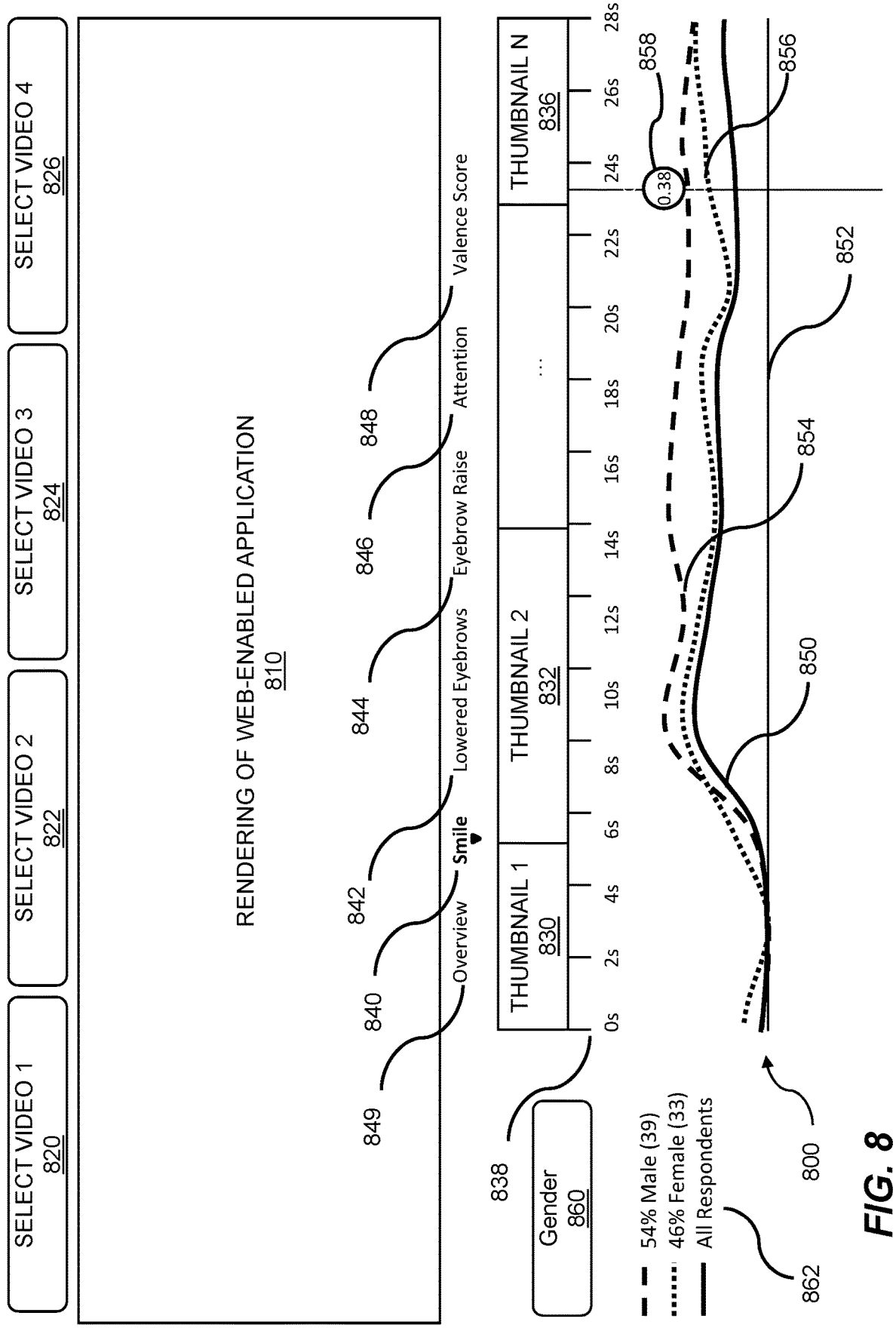
FIG. 8 is a graphical representation of mental state analysis.

The flow 300 may continue with uploading mental state information 330 to a server or other computing device. The server may be remote from the user and may be a host to data used by a social network, but in other embodiments the server may be separate from the social network's computer system and be used for storage for mental state information as well as other functionality. In some cases, an image may be communicated 340 to the server with the mental state information. The image may be of the individual as the mental state data was being collected and may be representative of the mental state information. In other embodiments, the image may be captured or identified in advance to represent a particular mental state. The flow 300 may continue with presenting the mental state information to the individual 350, prior to the individual electing to share mental state information 360. Some embodiments may allow the user to make the election before the presenting. In some embodiments the mental state data, the mental state information, or a subset of the mental state information may be presented to the individual. In some embodiments there may be no presentation. The mental state information may be presented to the individual in various ways such as a textual description of a mood, an image obtained of the individual or from the individual, a graph such as shown in FIG. 2 or FIG. 8, or another way of conveying the mental state information.

The flow 300 may continue with electing, by the individual, to share the mental state information 360 or mental states. The individual may choose to restrict distribution 362 of the mental state information. The individual may choose to share all or a portion of the mental state data and mental state information. The individual may choose to share with an individual, a group of people, or across a social network, such as restricting distribution of the mental state information to a subset of a social network. In embodiments, mental state information may be shared to others whom the network may recommend. In some embodiments, a reference to a web-enabled application may be forwarded 364 to the selected group or subgroup. In some embodiments, the forwarding is accomplished by selecting a "like" type button on a web page. The reference may include information on a video, trailer, e-book, web site, movie, advertisement, television show, streamed video clip, video game, computer game, or the like. The reference may include a timestamp, page number, web page URL, or the like to identify a portion of the reference. The forwarding may include a Twitter™ message, text, SMS, or the like. A URL or short-URL may be included when the reference is forwarded 364. The flow 300 may continue with sharing mental state information 370. The sharing may include transmission of data from an individual's client computer to a server which retains mental state information. The sharing may be directly from an individual's client computer to a social network website or application. The sharing may include a web link, a web-enabled application reference, or a web-enabled application. The mental state information may be communicated from the server to an individual 380. Alternatively, there may be peer-to-peer sharing of mental state information from a first individual to a second individual. Some embodiments may include sharing the mental state information across a social network 382. Mental states may be communicated via Facebook™, LinkedIn™, MySpace™, Twitter™, Google+™ or other social networking platforms.

Figure 4:
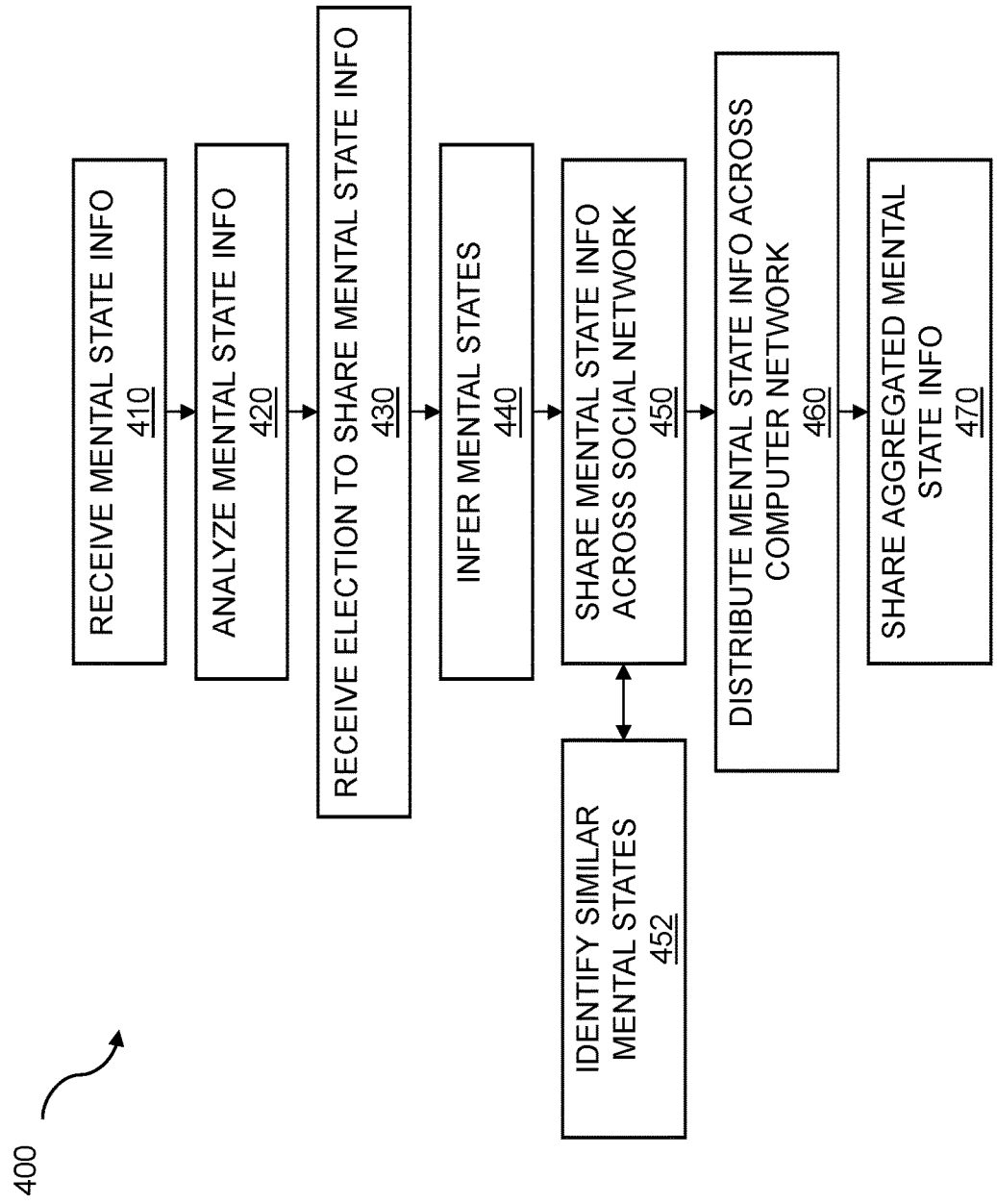
FIG. 4 is a flow diagram for sharing across a social network.

FIG. 4 is a flow diagram for sharing across a social network. The flow 400 describes a computer implemented method for sharing mental states and may represent activity from a server perspective. The flow 400 may begin with receiving mental state data 410 on an individual. The mental state information may be collected as described for flow 300, or may be received from a client computer that collected the mental state information. In some embodiments, the mental state information may be analyzed 420 to extract further information such as facial expressions, action units, head gestures, smiles, brow furrows, squints, lowered eyebrows, raised eyebrows, or attention. An election to share mental state information may be received 430 from the individual to indicate their desire to share the mental state information with others. The election may come from a user selecting a button on a screen of a web-enabled application to opt-in to sharing mental state information.

The flow 400 continues with inferring mental states 440 for the individual based on the mental state information which was received. The mental states that may be inferred include frustration, confusion, disappointment, hesitation, cognitive overload, focusing, being engaged, attending, boredom, exploration, confidence, trust, delight, and satisfaction. In some embodiments, collective mental states may be inferred for a group of people. The flow 400 continues with sharing the inferred mental states across a social network 450. Some embodiments may include identifying similar mental states within the social network 452. The group of people that may be searched to identify similar mental states may vary according to the embodiment. Some embodiments may only search an individual's direct contact list while others may search an extended contact list such as including the contacts of the individual's contacts, or an even more extended group going out several levels of contact's contacts. In other embodiments, only a group that has been specifically created to share mental state information may be searched while other embodiments may search outside of the individual's extended network to help identify people that may be interesting to the individual and may be potential new contacts.

Multiple individuals can have their mental states collected and their mental state information distributed across a computer network 460 for various purposes. These mental states can be aggregated together and the combined mental state evaluation can be posted or propagated to others. A webmaster may collect affect data and mental state information. This data and/or information can be tagged to the website controlled by the webmaster and therefore the mental states can be associated with the web-enabled application. Further, aggregated responses can be used to evaluate the viral potential of a web-enabled application, such as a video or game. The aggregation may take various forms in various embodiments but examples may include creating an aggregate mood of an individual's contact on a social network, creating aggregate mental state information of the people that have viewed a movie trailer, tabulating a percentage of a particular group having a particular mental state, or any other method of aggregating mental state information. Flow 400 may include sharing aggregated mental state information across a social network 470. Sharing across a social network may include automatic sharing to one or more social websites, social applications, and so on.

Figure 5:
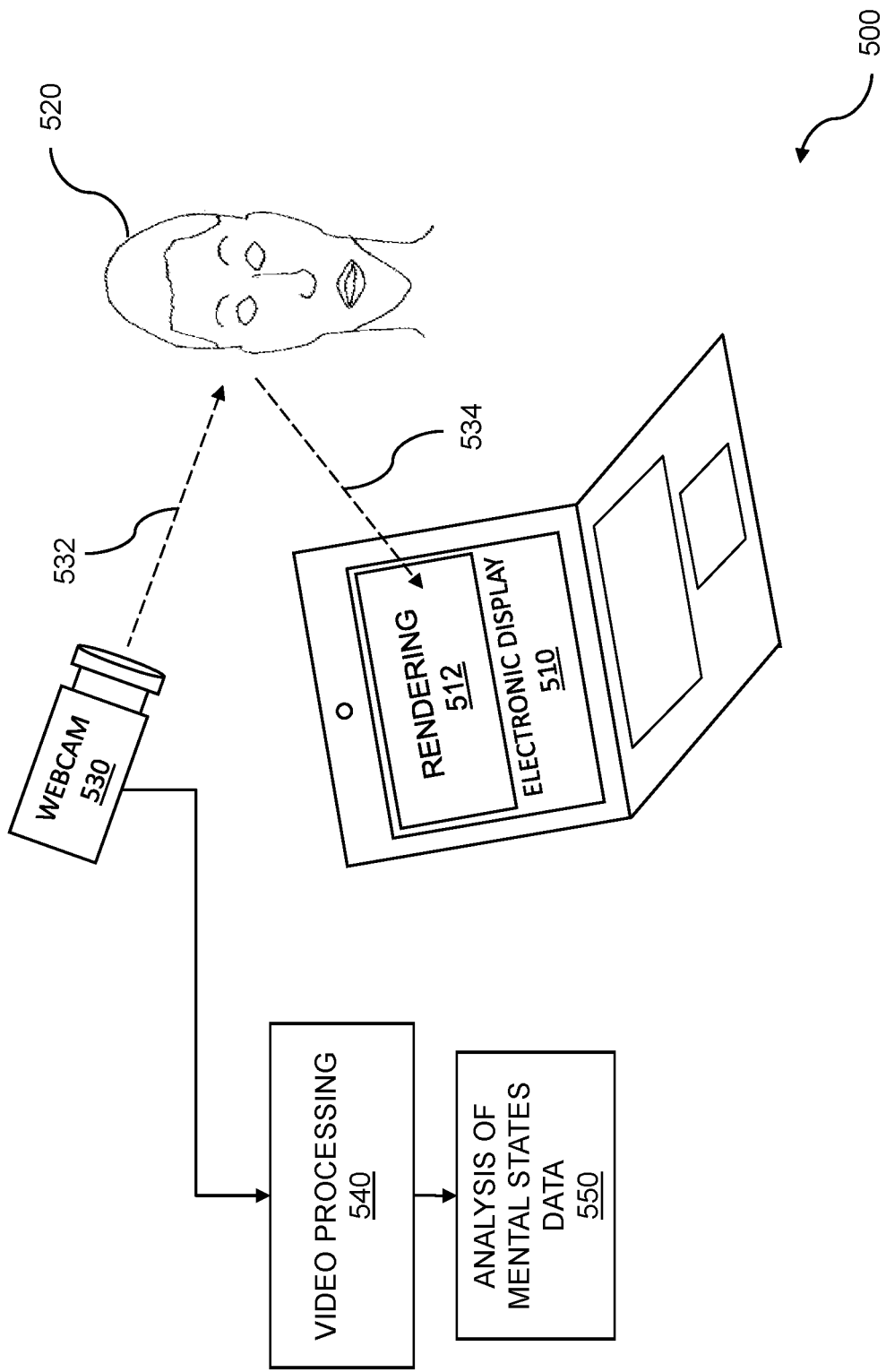
FIG. 5 is a diagram for capturing facial response to rendering.

FIG. 5 is a diagram for capturing facial response to a rendering. In system 500, an electronic display 510 may show a rendering 512 to a person 520 in order to collect facial data and/or other indications of their mental state. A webcam 530, connected to a computing device, is used to capture one or more of the facial data and the physiological data. The facial data may include information on facial expressions, action units, head gestures, smiles, brow furrows, squints, lowered eyebrows, raised eyebrows, or attention in various embodiments. The webcam 530 may capture video, audio, and/or still images of the person 520. A webcam, as the term is used herein and in the claims, may be a video camera, still camera, thermal imager, CCD device, phone camera, three-dimensional camera, a depth camera, multiple webcams 530 used to show different views of the person 520 or any other type of image capture apparatus that may be connected to, and allow data captured to be used in, a computing device in a real-time or near-real-time manner. The electronic display 510 may be any electronic display, including but not limited to, a computer display, a laptop screen, a net-book screen, a tablet computer, a cell phone display, a mobile device display, a remote with a display, or some other electronic display. The rendering 512 may be that of a web-enabled application and may include a landing page, a checkout page, a webpage, a website, a web-enabled application, a video on a web-enabled application, a game on a web-enabled application, a trailer, a movie, an advertisement, or a virtual world or some other output of a web-enabled application. The rendering 512 may also be a portion of what is displayed, such as a button, an advertisement, a banner ad, a drop-down menu, and a data element on a web-enabled application or other portion of the display. In some embodiments the webcam 530 may observe 532 the person to collect facial data. The facial data may include information on action units, head gestures, smiles, brow furrows, squints, lowered eyebrows, raised eyebrows, and attention. Additionally, the eyes may be tracked to identify a portion of the rendering 512 on which they are focused. For the purposes of this disclosure and claims, the word "eyes" may refer to either one or both eyes of an individual, or to any combination of one or both eyes of individuals in a group. The eyes may move as the rendering 512 is observed 534 by the person 520. The images of the person 520 from the webcam 530 may be captured by a video processing unit 540, which may provide computer-based processing of the images into mental state data. For example, a webcam image of a person with raised lip corners may be processed to determine the mental state data of the presence of a smile. The meaning of the smile at this point is ambiguous, because a smile may be real, it may be fake, it may be polite, and so on; further analysis is required to determine an actual mental state. In some embodiments, video may be captured, while in others, a series of still images may be captured. The captured video or still images may be used in one or more analyses.

Analysis of action units, gestures, and mental state data 550 may be accomplished using the captured images of the person 520. The action units may be used to identify smiles, frowns, and other facial indicators of mental states. The gestures, including head gestures, may indicate interest or curiosity. For example, a head gesture of moving toward the electronic display 510 may indicate increased interest or a desire for clarification. Based on the captured images, analysis of physiological data may be performed. Respiration, heart rate, heart rate variability, perspiration, temperature, and other physiological indicators of mental state can be observed by analyzing the images. So in various embodiments, a webcam is used to capture one or more of the facial data and the physiological data.

Figure 6:
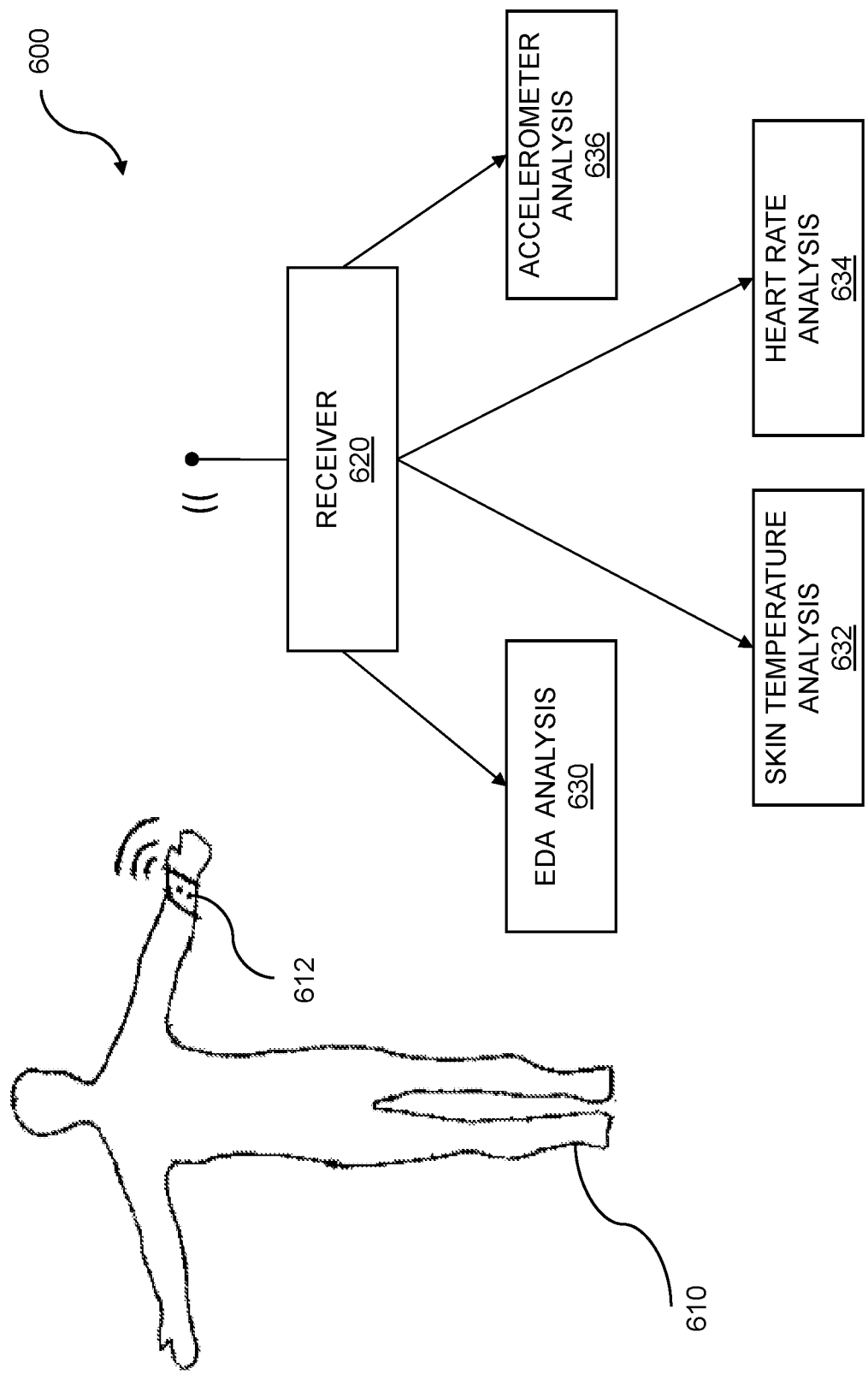
FIG. 6 is a diagram representing physiological analysis.

FIG. 6 is a diagram representing physiological analysis. A system 600 may analyze a person 610 for whom data is being collected. The person 610 may have a biosensor 612 attached to him or her so that the mental state data is collected using a biosensor 612. The biosensor 612 may be placed on the wrist, palm, hand, head, or other part of the body. In some embodiments, multiple biosensors may be placed on the body in multiple locations. The biosensor 612 may include detectors for physiological data, such as electrodermal activity, skin temperature, accelerometer readings, and the like. Other detectors for physiological data may be included as well, such as heart rate, blood pressure, EKG, EEG, further brain waves, and other physiological detectors. The biosensor 612 may transmit information collected to a receiver 620 using wireless technology such as Wi-Fi, Bluetooth®, 802.11, cellular, or other bands. In other embodiments, the biosensor 612 may communicate with the receiver 620 by other methods such as a wired interface, or an optical interface. The receiver may provide the data to one or more components in the system 600. In some embodiments, the biosensor 612 may record various physiological information in memory for later download and analysis. In some embodiments, the download of data the recorded physiological information may be accomplished through a USB port or other wired or wireless connection.

Mental states may be inferred based on physiological data, such as physiological data from the sensor 612. Mental states may also be inferred based on facial expressions and head gestures observed by a webcam or a combination of data from the webcam along with data from the sensor 612. The mental states may be analyzed based on arousal and valence. Arousal can range from being highly activated, such as when someone is agitated, to being entirely passive, such as when someone is bored. Valence can range from being very positive, such as when someone is happy, to being very negative, such when someone is angry. Physiological data may include electrodermal activity (EDA) or skin conductance or galvanic skin response (GSR), accelerometer readings, skin temperature, heart rate, heart rate variability, and other types of analysis of a human being. It will be understood that both here and elsewhere in this document, physiological information can be obtained either by biosensor 612 or by facial observation. Facial data may include facial actions and head gestures used to infer mental states. Furthermore, the data may include information on hand gestures or body language and body movements such as visible fidgets. In some embodiments these movements may be captured by cameras or by sensor readings. Facial data may include the tilting the head to the side, leaning forward, a smile, a frown, as well as many other gestures or expressions.

Electrodermal activity may be collected in some embodiments and may be collected continuously, every second, four times per second, eight times per second, 32 times per second, or on some other periodic basis. The electrodermal activity may be recorded. The recording may be to a disk, a tape, onto flash memory, into a computer system, or streamed to a server. The electrodermal activity may be analyzed 630 to indicate arousal, excitement, boredom, or other mental states based on changes in skin conductance. Skin temperature may be collected on a periodic basis and may be recorded. The skin temperature may be analyzed 632 and may indicate arousal, excitement, boredom, or other mental states based on changes in skin temperature. The heart rate may be collected and recorded. The heart rate may be analyzed 634 and a high heart rate may indicate excitement, arousal, or other mental states. Accelerometer data may be collected and indicate one, two, or three dimensions of motion. The accelerometer data may be recorded. The accelerometer data may be used to create an actigraph showing an individual's activity level over time. The accelerometer data may be analyzed 636 and may indicate a sleep pattern, a state of high activity, a state of lethargy, or other state based on accelerometer data. The various data collected by the biosensor 612 may be used along with the facial data captured by the webcam.

Figure 7:
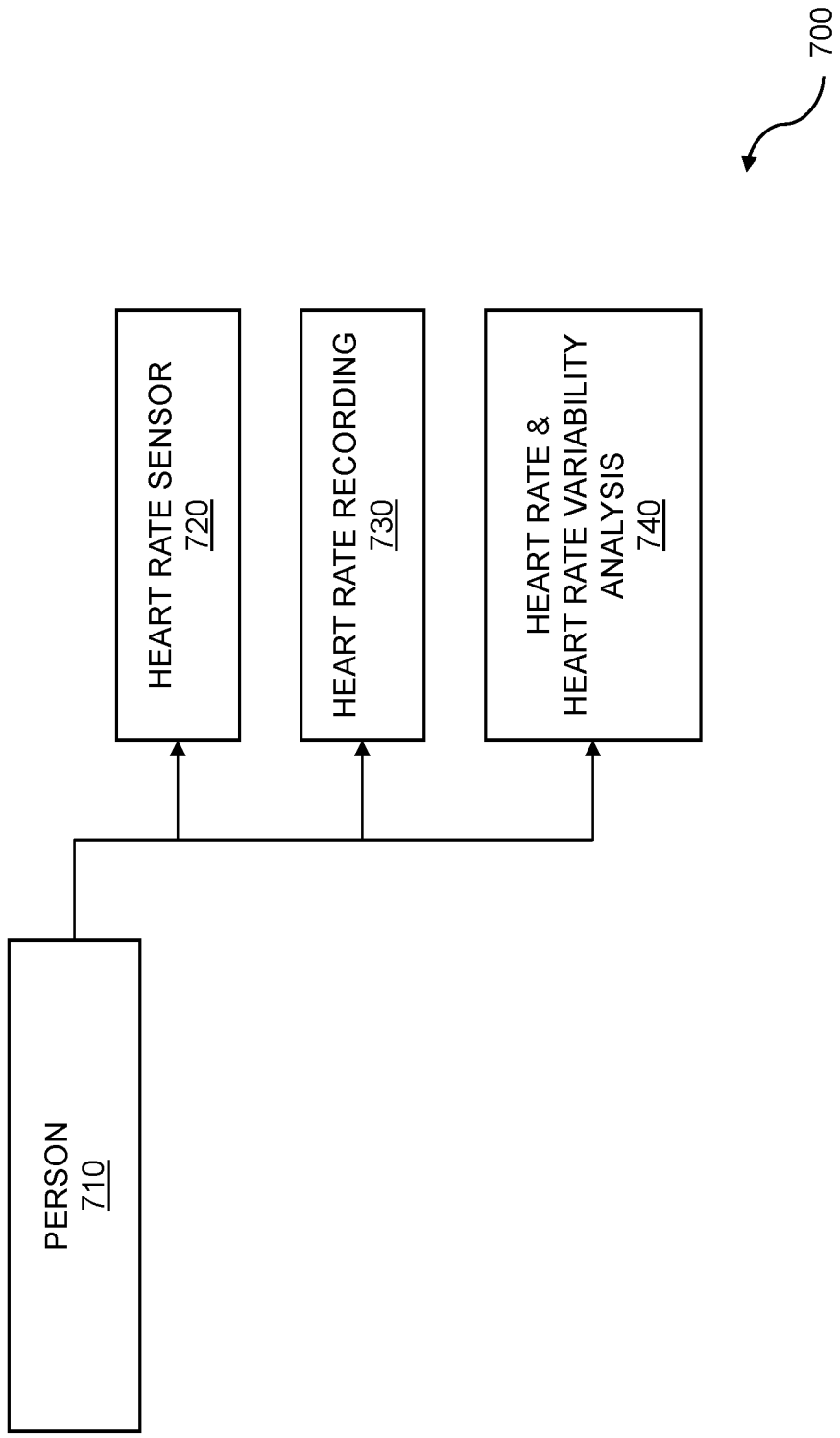
FIG. 7 is a diagram of heart related sensing.

FIG. 7 is a diagram of heart related sensing. A person 710 is observed by system 700 which may include a heart rate sensor 720, a specific type of biosensor. The observation may be through a contact sensor or through video analysis, which enables capture of heart rate information, or other contactless sensing. In some embodiments, a webcam is used to capture the physiological data. In some embodiments, the physiological data is used to determine autonomic activity, and the autonomic activity may be one of a group comprising heart rate, respiration, and heart rate variability in some embodiments. Other embodiments may determine other autonomic activity such as pupil dilation or other autonomic activities. The heart rate may be recorded 730 to a disk, a tape, into flash memory, into a computer system, or streamed to a server. The heart rate and heart rate variability may be analyzed 740. An elevated heart rate may indicate excitement, nervousness, or other mental states. A lowered heart rate may indicate calmness, boredom, or other mental states. The level of heart-rate variability may be associated with fitness, calmness, stress, and age. The heart-rate variability may be used to help infer the mental state.

High heart-rate variability may indicate good health and lack of stress. Low heart-rate variability may indicate an elevated level of stress. Thus, physiological data can include one or more of electrodermal activity, heart rate, heart rate variability, skin temperature, and respiration.

FIG. 8 is a graphical representation of mental state analysis. A window 800 may be shown which includes, for example, rendering of the web-enabled application 810 having associated mental state information. The rendering in the example shown is a video but may be any other sort of rendering in other embodiments. A user may be able to select between a plurality of renderings using various buttons and/or tabs such as Select Video 1 button 820, Select Video 2 button 822, Select Video 3 button 824, and Select Video 4 button 826. Various embodiments may have any number of selections available for the user and some may be other types of renderings instead of video. A set of thumbnail images for the selected rendering, that in the example shown include thumbnail 1 830, thumbnail 2 832, through thumbnail N 836, may be shown below the rendering along with a timeline 838. Some embodiments may not include thumbnails, or have a single thumbnail associated with the rendering, and various embodiments may have thumbnails of equal length while others may have thumbnails of differing lengths. In some embodiments, the start and/or end of the thumbnails may be determined by the editing cuts of the video of the rendering while other embodiments may determine a start and/or end of the thumbnails based on changes in the captured mental states associated with the rendering. In embodiments, thumbnails of the person on whom mental state analysis is being performed may be displayed.

Some embodiments may include the ability for a user to select a particular type of mental state information for display using various buttons or other selection methods. In the example shown, the smile mental state information is shown as the user may have previously selected the Smile button 840. Other types of mental state information that may be available for user selection in various embodiments may include the Lowered Eyebrows button 842, Eyebrow Raise button 844, Attention button 846, Valence Score button 848, or other types of mental state information, depending on the embodiment. The mental state information displayed may be based on physiological data, facial data, and actigraphy data. An Overview button 849 may be available to allow a user to show graphs of the multiple types of mental state information simultaneously.

Because the Smile option 840 has been selected in the example shown, smile graph 850 may be shown against a baseline 852 showing the aggregated smile mental state information of the plurality of individuals from whom mental state data was collected for the rendering 810. Male smile graph 854 and female smile graph 856 may be shown so that the visual representation displays the aggregated mental state information on a demographic basis. The various demographic based graphs may be indicated using various line types as shown or may be indicated using color or other method of differentiation. A slider 858 may allow a user to select a particular time of the timeline and show the value of the chosen mental state for that particular time. The slider may show the same line type or color as the demographic group whose value is shown.

Various types of demographic based mental state information may be selected using the demographic button 860 in some embodiments. Such demographics may include gender, age, race, income level, or any other type of demographic including dividing the respondents into those respondents that had a higher reaction from those with lower reactions. A graph legend 862 may be displayed indicating the various demographic groups, the line type or color for each group, the percentage of total respondents and or absolute number of respondents for each group, and/or other information about the demographic groups. The mental state information may be aggregated according to the demographic type selected.

Figure 9:
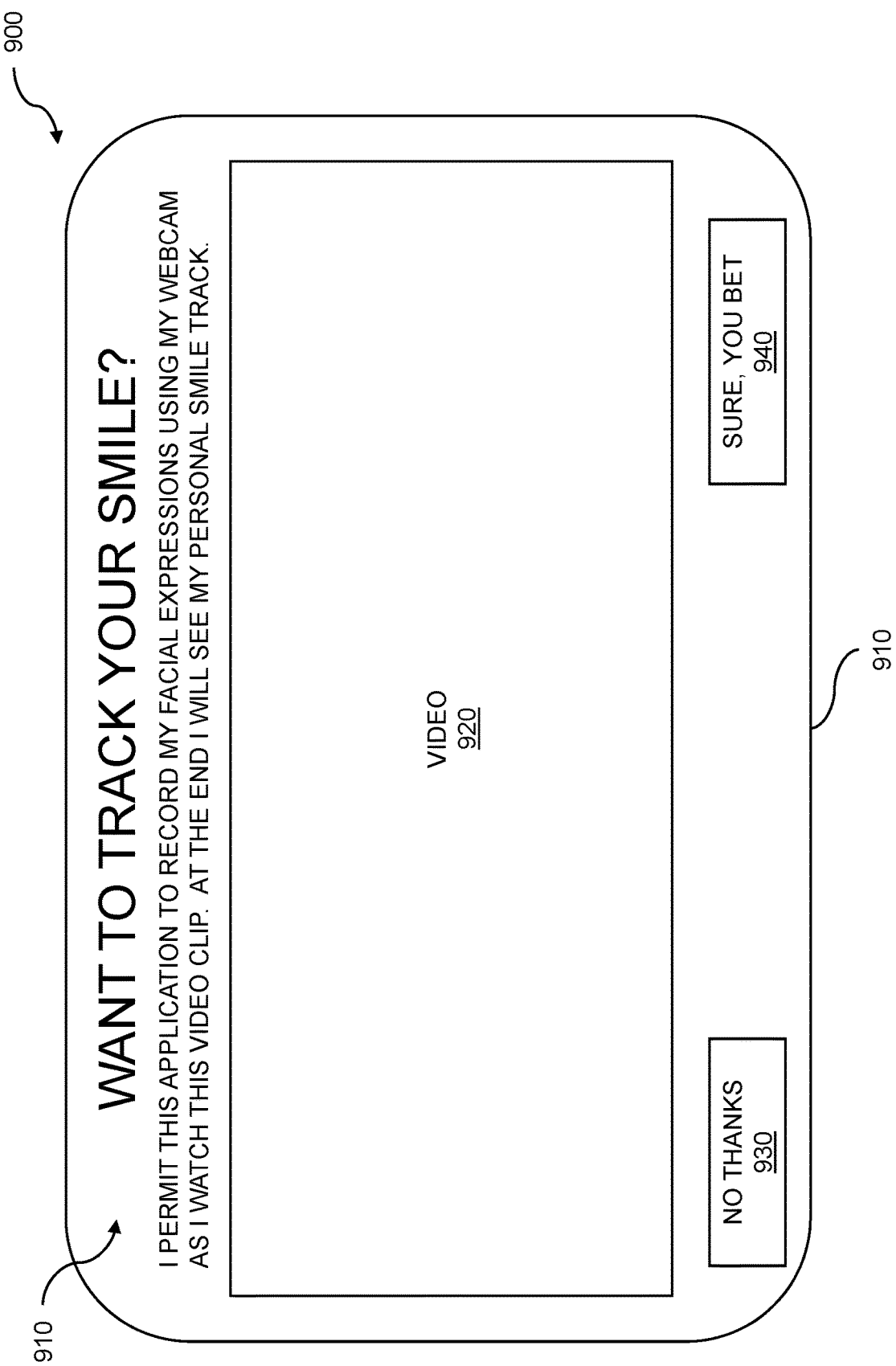
FIG. 9 is a diagram of a web page to elect sharing.

FIG. 9 is a diagram of a web page to elect sharing. A rendering 900 from a web-enabled application may present an individual with an option to collect mental state information. Flash™ may be used in some implementations to present and/or ask for permission. Various embodiments may use different language to ask the individual for their permission. In the embodiment shown, text 910 representing an individual's permission for the web-enabled application to record facial expressions is presented to the individual. A video 920 may be displayed to the individual. The video 920 may be the video from the individual's webcam, content that the individual will react to, a message asking the individual's permission, or any other video. Some embodiments may not include video but only include text or include text and images. The individual may respond to the invitation by clicking one of at least two buttons. If the individual does not want to be recorded and share their mental state information, the individual may click on the "No Thanks" button 930, and no mental state information will be captured of the individual. If the individual wants to be recorded and share their mental state information, the individual may click on the "Sure, You Bet" button 940 to initiate capture of their mental state information. Various embodiments may use other language for the buttons and some embodiments may include more than 2 options, such as including an option to share mental state information only with a specific group, capture facial data but don't share the mental state information until the individual has reviewed the mental state information, or various other restrictions on the mental state information. So sharing the mental state information may include electing, by the individual, to share the mental state information.

Figure 10:
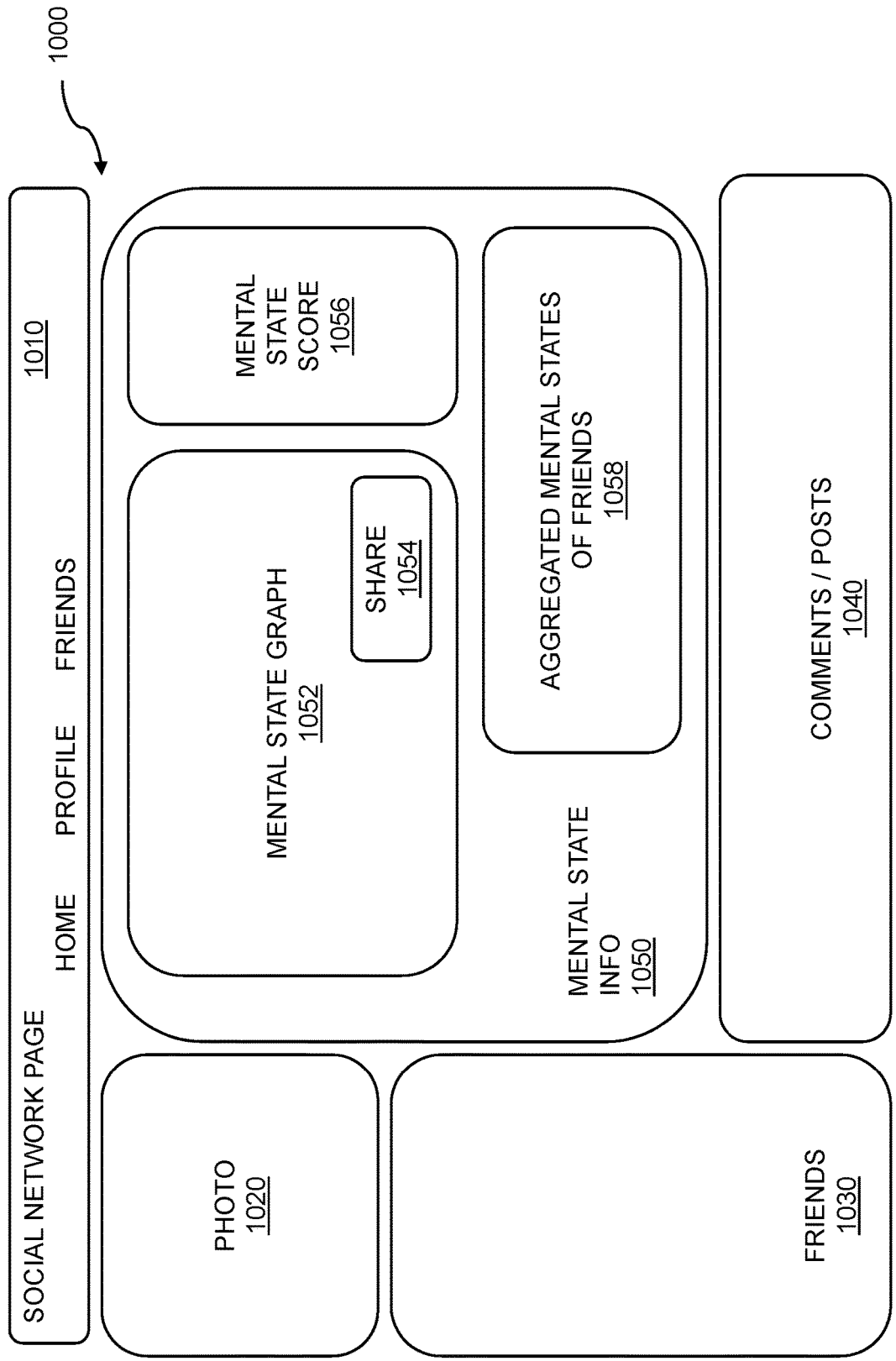
FIG. 10 is an example social network page content.

FIG. 10 is an example social network page content 1000. The exact content and formatting may vary between social networks but similar content may be formatted for a variety of social networks including, but not limited to, a blogging website, Facebook™ LinkedIn™, MySpace™, Twitter™, Google+™, or any other social network. A social network page for a particular social network may include one or more of the components shown in the social network page content 1000, but may include various other components in place of, or in addition to, the components shown. The social network content 1000 may include a header 1010 that may identify the social network and may include various tabs or buttons for navigating the social network site, such as the "HOME," "PROFILE," and "FRIENDS" tabs shown. The social network content 1000 may also include a profile photo 1020 of the individual that owns the social network content 1000. Various embodiments may include a friends list 1030 showing the contacts of the individual on the particular social network. Some embodiments may include a comments component 1040 to show posts from the individual, friends, or other parties.

The social network content 1000 may include mental state information section 1050. The mental state information section 1050 may allow for posting mental state information to a social network web page. It may include mental state information that has been shared by the individual or may include mental state information that has been captured but not yet shared, depending on the embodiment. In at least one embodiment, a mental state graph 1052 may be displayed to the individual showing their mental state information while viewing a web-enabled application, such as the graph of FIG. 2. If the information has not yet been shared over the social network, a share button 1054 may be included in some embodiments. If the individual clicks on the share button 1054, mental state information, such as the mental state graph 1052 or various summaries of the mental state information, may be shared over the social network. The mental state information may be shared with an individual, a group or subgroup of contacts or friends, another group defined by the social network, or may be open to anyone, depending on the embodiment and a selection of the individual. The photo 1020, or another image shown on the social network, may be updated with an image of the individual with the mental state information that is being shared, such as a smiling picture if the mental state information is happy. In some cases, the image of the individual is from a peak time of mental state activity. In some embodiments, the photo 1020 section, or some other section of the social network page content 1000, may allow for video and the image includes a video of the individual's reaction or representing the mental state information. If the mental state information shared is related to a web-enabled application, forwarding a reference to the web-enabled application as a part of the sharing of the mental state information may be done, and may include a URL and a timestamp which may indicate a specific point in a video. Other embodiments may include an image of material from the web-enabled application or a video of material from the web-enabled application. The forwarding, or sharing, of the various mental state information and related items may be done on a single social network, or some items may be forwarded on one social network while other items are forwarded on another social network. In some embodiments, the sharing is part of a rating system for the web-enabled application, such as aggregating mental state information from a plurality of users to automatically generate a rating for videos.

Some embodiments may include a mental state score 1056. In some embodiments, mental state data is collected over a period of time and the analyzed mental state information that is shared is a reflection of a mood for the individual in a mental state score 1056. The mental state score may be a number, a sliding scale, a colored scale, various icons or images representing moods or any other type of representation. In some embodiments, the mental state score 1056 may emulate a "mood ring" as was popular back in the 1970's. Various moods may be represented, including, but not limited to, frustration, confusion, disappointment, hesitation, cognitive overload, focusing, being engaged, attending, boredom, exploration, confidence, trust, delight, and satisfaction.

Some embodiments may include a section for aggregated mental states of friends 1058. This section may include an aggregated mood of those friends shown in the friends list section 1030 that have opted to share their mental state information. Other embodiments may include aggregated mental states of those friends that have viewed the same web-enabled application as the individual and may allow the individual to compare their mental state information in the mental state graph 1052 to their friends' mental state information 1058. Other embodiments may display various aggregations of different groups.

Figure 11:
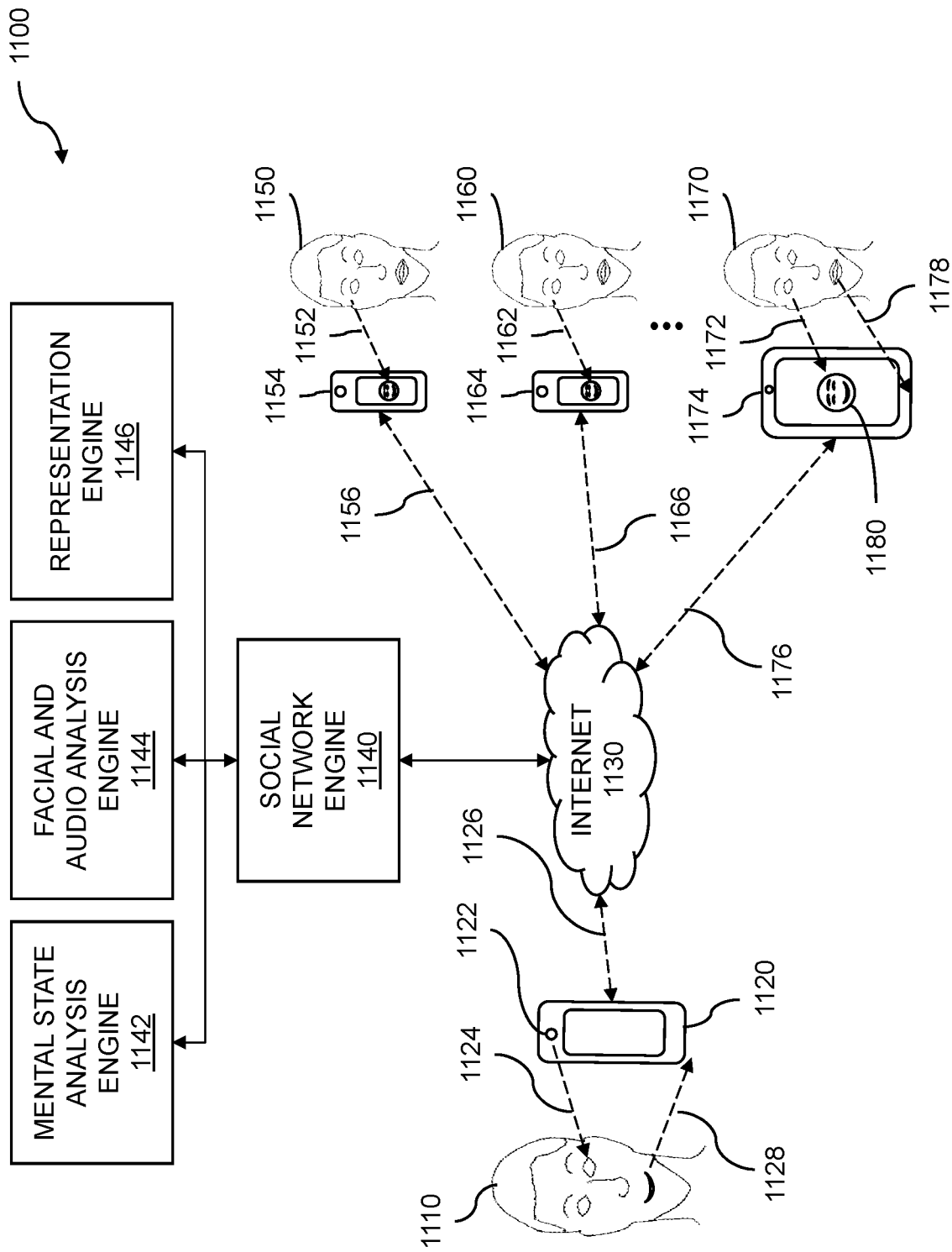
FIG. 11 shows communication of mental states using a social network.

FIG. 11 shows communication of mental states using a social network. Sharing affect across a social network can include communicating mental states across the social network. Mental state data is collected from an individual. The mental state data can be collected over a period of time. The mental state data is analyzed to produce mental state information. The mental state information is shared across a social network. The mental state information that is shared can be a reflection of a mood for the individual. The mood can include one of a group including frustration, confusion, disappointment, hesitation, cognitive overload, focusing, being engaged, attending, boredom, exploration, confidence, trust, delight, and satisfaction. The individual can elect to share the mental state information. The mental state information is presented to the individual prior to the electing to share.

In the diagram 1100, mental state of an individual can be communicated to friends, colleagues, followers, etc., using a social network. The mental state information that is shared can be a reflection of a mood for the individual. The mood can be communicated using a representative icon. The representative icon can be an emoji. In embodiments, the mood can include one of a group including frustration, confusion, disappointment, hesitation, cognitive overload, focusing, being engaged, attending, boredom, exploration, confidence, trust, delight, and satisfaction. In further embodiments, the mental state information is presented to the individual prior to them electing to share it. Based on the social network over which the individual shares her or his mental state information, the individual can elect to opt-in to share the mental state information, representations of the mental state information, and so on. The representations of the mental state information can include one or more emoji. The communication of mental states, moods, and so on, using a social network, can be facilitated by a video capture device, an audio capture device, a local server, a remote server, a cloud server, an app running on a portable, network-enabled electronic device, a semiconductor-based logic device, and so on. The communicating can include live streaming of audio and video, representations of moods and mental states, etc. Social networks can include Facebook™ Google+™, Twitter™, Instagram™, Snapchat™ and the like. Depending on the social network used, viewers of the communicated mental states can comment on the mental states by adding text, "liking", tweeting, or otherwise react to the mental states.

The example 1100 shows a user 1110 communicating one or more of mental states, representations of mental states, moods, representations of moods, and so on, to one or more people as shown by the person 1150, the person 1160, and the person 1170. The people to whom the communicating is provided can be friends, colleagues, followers, and so on. A portable, network-enabled, electronic device 1120 can be coupled to a front-side camera 1122. The portable, network-enabled, electronic device 1120 can be coupled to a microphone (not shown). The portable electronic device 1120 can be a smartphone, a PDA, a tablet, a laptop computer, and so on. The camera 1122 coupled to the device 1120 can have a line-of-sight view 1124 to the user 1110 and can capture video of the user 1110. The microphone coupled to the device 1120 can collect audio 1128 of the user 1110. The captured video and audio can be sent to a social network engine 1140 using a network link 1126 to the Internet 1130. The network link can be a wireless link, a wired link, a hybrid link combining wired and wireless links, and so on.

The social network engine 1140 can be coupled to a mental state analysis engine 1142. The mental state analysis engine 1142 can analyze mental states of the user 1110 and can identify moods of the user that are reflected by the mental states. The moods of the user can include one of a group comprising frustration, confusion, disappointment, hesitation, cognitive overload, focusing, being engaged, attending, boredom, exploration, confidence, trust, delight, and satisfaction. The social network engine 1140 can be coupled to a facial and audio analysis engine 1144. The facial and audio analysis engine can analyze captured facial data and audio data to determine one or more mental states of the individual. The captured facial data can be analyzed using the facial action coding system (FACS). The FACS encodes movements of individual muscles of the face, and determines mental states based on the movements of the muscles. The captured audio data can be analyzed to determine information and meaning from audio signals. The analysis of the audio data can include tone, cadence, prosody, etc., and can be used to determine mental states. The social network engine 1140 can be coupled to a representation engine 1146. The representation engine 1146 can take mental states from the mental state analysis engine 1142, and facial and audio analysis from the facial and audio analysis engine 1144, and determine one or more representations of mental states, moods, emotional states, and so, of the individual. The mental states, moods, emotional states, etc., can be represented by emoji, emoticons, cartoons, pictograms, animations, graphics interchange format (GIF) files, and so on. The one or more representations can be used to communicate mental states of the individual using a social network. In the example 1100, a representation, or emoji, 1180 can be chosen and rendered on the displays coupled to the electronic devices 1154, 1164, 1174, and so on. The emoji 1180 can represent a smile determined by analyzing mental state data collected from the individual, or user, 1110.

In the example 1100, the user 1110 has three followers: the person 1150, the person 1160, and the person 1170. Each follower has a line-of-sight view to a video screen on a portable, networked electronic device. In other embodiments, one or more followers follow the user 1110 using any other networked electronic device, including a computer. In the example 1100, the person 1150 has a line-of-sight view 1152 to the video screen of a device 1154; the person 1160 has a line-of-sight view 1162 to the video screen of a device 1164, and the person 1170 has a line-of-sight view 1172 to the video screen of a device 1174. The portable electronic devices 1154, 1164, and 1174 can each be a smartphone, a PDA, a tablet, and so on. Each portable device can receive communicated mental states of the user 1110 through the Internet 1130 using a social networking app and/or social networking platform. The device 1154 can receive communicated mental states using the network link 1156, the device 1164 can receive communicated mental states using the network link 1166, the device 1174 can receive communicated mental states using the network link 1176, and so on. The network link can be a wireless link, a wired link, a hybrid link, and so on. Depending on the social networking app and/or platform, and the electronic device, used by the one or more followers, such as the person, or followers, 1150, 1160, 1170, and so on, the followers can reply to, comment on, and otherwise provide feedback to the user 1110 using their devices 1154, 1164, and 1174, respectively. A person, or follower, 1170 can produce audio 1178 that can be collected by her or his device 1174. The produced audio can include speech, vocalizations, and so on, and can be in response to the representation 1180 presented on the screen coupled to electronic device 1174. The collected audio can be shared with the individual person, or user, 1110.

Figure 12:
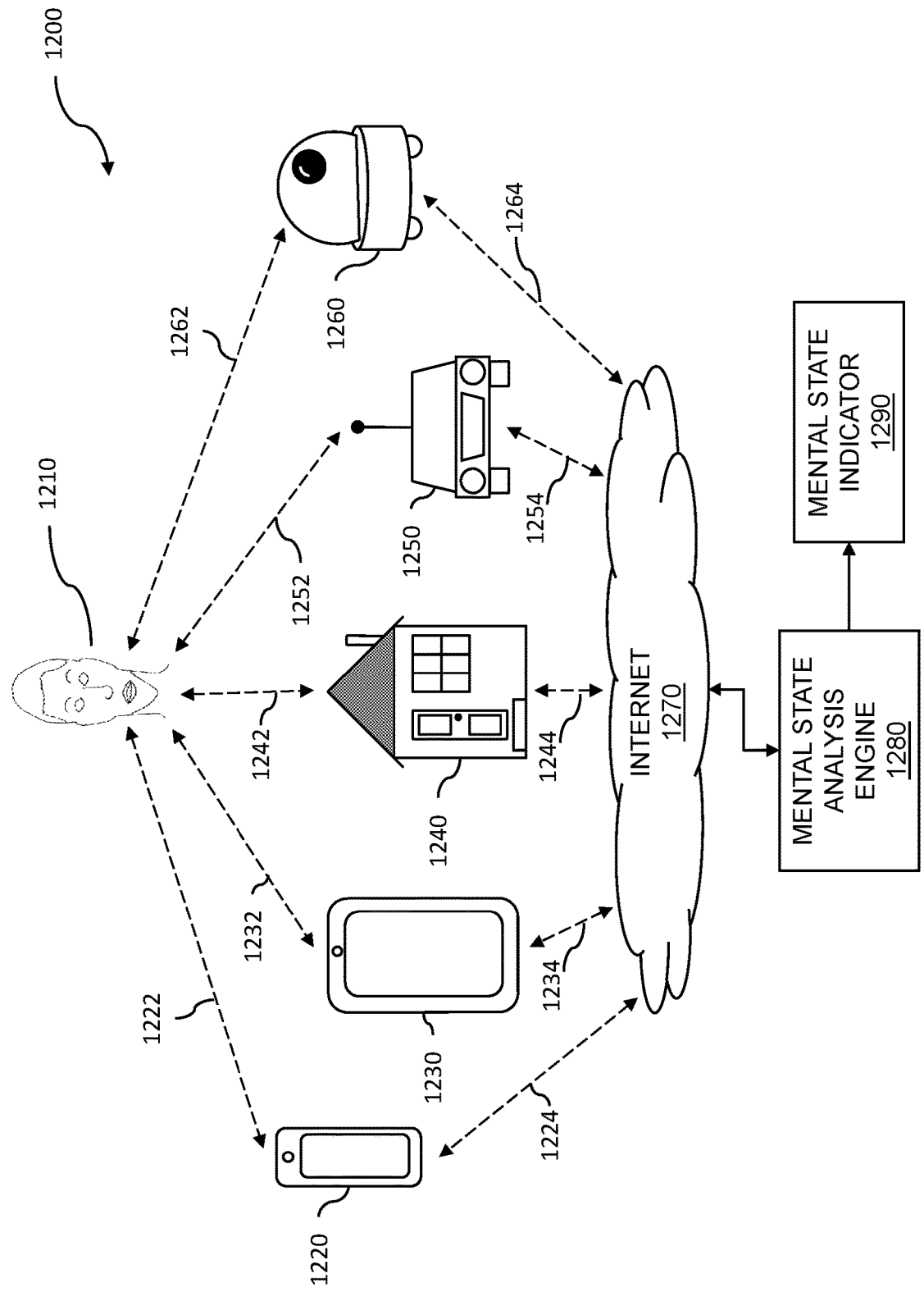
FIG. 12 illustrates image collection including devices and locations.

FIG. 12 illustrates image collection including devices and locations. Images can be collected for sharing affect across a social network. Mental state data is collected from an individual. The mental state data is analyzed to produce mental state information. The mental state information is shared across a social network. The individual can elect to share the mental state information. The mental state information is presented to the individual prior to the electing. In the diagram 1200, the multiple mobile devices, vehicles, and locations, can be used singly or together to collect video data on a user 1210. While one person is shown, the video data can be collected on multiple people. A user 1210 can be observed as she or he is performing a task, experiencing an event, viewing a media presentation, and so on. The user 1210 can be shown one or more media presentations, political presentations, social media, or another form of displayed media. The one or more media presentations can be shown to a plurality of people. The media presentations can be displayed on an electronic display coupled to a client device. The data collected on the user 1210 or on a plurality of users can be in the form of one or more videos, video frames, still images, etc. The plurality of videos can be of people who are experiencing different situations. Some example situations can include the user or plurality of users being exposed to TV programs, movies, video clips, social media, social sharing, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1210 can be analyzed and viewed for a variety of purposes including expression analysis, mental state analysis, and so on. The electronic display can be on a smartphone 1220 as shown, a tablet computer 1230, a personal digital assistant, a television, a mobile monitor, or any other type of electronic device. In one embodiment, expression data is collected on a mobile device such as a computer-enabled, or smart, cell phone 1220, a tablet computer 1230, a laptop computer, or a watch. Thus, the multiple sources can include at least one mobile device, such as a smartphone 1220 or a tablet 1230, or a wearable device such as a watch or glasses (not shown). A mobile device can include a front-side camera and/or a back-side camera that can be used to collect expression data. Sources of expression data can include a webcam, a phone camera, a tablet camera, a wearable camera, and a mobile camera. A wearable camera can comprise various camera devices, such as a watch camera. In addition to using client devices for data collection from the user 1210, data can be collected in a house 1240 using a web camera connected to a computing device, or the like; in a vehicle 1250 using a web camera connected to a computing device, a client device, etc.; by a social robot 1260, and so on.

As the user 1210 is monitored, the user 1210 might move due to the nature of the task, boredom, discomfort, distractions, or for another reason. As the user moves, the camera with a view of the user's face can be changed. Thus, as an example, if the user 1210 is looking in a first direction, the line of sight 1222 from the smartphone 1220 is able to observe the user's face, but if the user is looking in a second direction, the line of sight 1232 from the tablet 1230 is able to observe the user's face. Furthermore, in other embodiments, if the user is looking in a third direction, the line of sight 1242 from a camera in the house 1240 is able to observe the user's face, and if the user is looking in a fourth direction, the line of sight 1252 from the camera in the vehicle 1250 is able to observe the user's face. If the user is looking in a fifth direction, the line of sight 1262 from the social robot 1260 is able to observe the user's face. If the user is looking in a sixth direction, a line of sight from a wearable watch-type device, with a camera included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1210 can also use a wearable device including a camera for gathering contextual information and/or collecting expression data on other users. Because the user 1210 can move her or his head, the facial data can be collected intermittently when she or he is looking in a direction of a camera. In some cases, multiple people can be included in the view from one or more cameras, and some embodiments include filtering out faces of one or more other people to determine whether the user 1210 is looking toward a camera. All or some of the expression data can be continuously or sporadically available from the various devices and other devices.

The captured video data can include facial expressions and can be transferred over the Internet 1270. The smartphone 1220 can share video using link 1224, the tablet 1230 using link 1234, the house 1240 using link 1244, the vehicle 1250 using link 1254, and the social robot 1260 using link 1264. The links 1224, 1234, 1244, 1254, and 1264 can be wired, wireless, and hybrid links. The captured video data, including facial expressions, can be analyzed on a mental state analysis engine 1280, on a computing device such as the video capture device, or on another separate device. The analysis could take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capture device. The analysis data from the mental state analysis engine can be processed by a mental state indicator 1290. The mental state indicator 1290 can indicate mental states, moods, emotions, etc. In embodiments, the emotions can include of one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, sadness, poignancy, or mirth.

Figure 13:
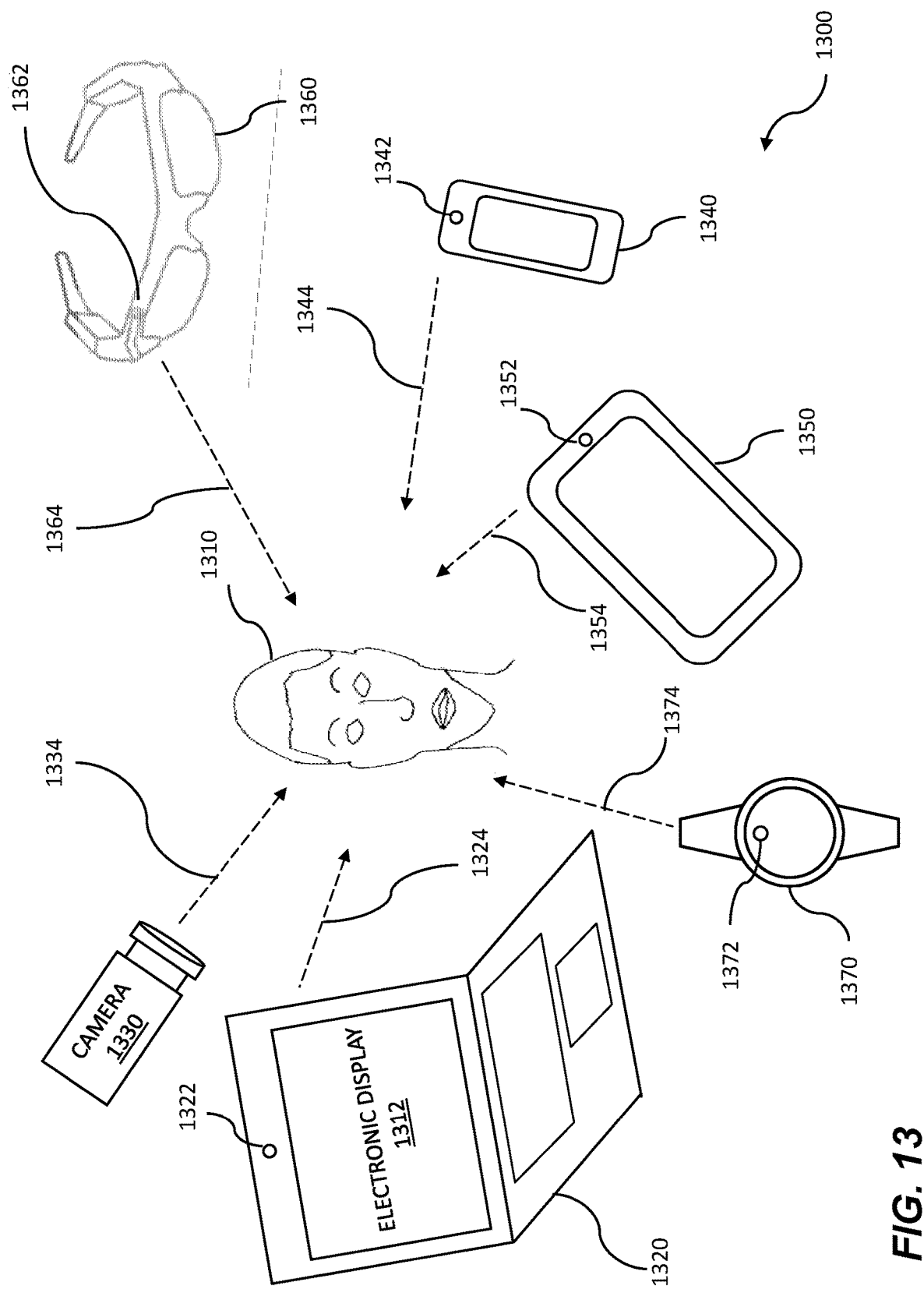
FIG. 13 is a diagram showing image collection including multiple mobile devices.

FIG. 13 is a diagram showing image collection including multiple mobile devices. The collected images can be analyzed for sharing affect across a social network. Mental state data is collected from an individual. The mental state data can be collected over a period of time. The mental state data is analyzed to produce mental state information. The mental state information is shared across a social network. The mental state information that is shared can be a reflection of a mood for the individual. The mood can include one of a group including frustration, confusion, disappointment, hesitation, cognitive overload, focusing, being engaged, attending, boredom, exploration, confidence, trust, delight, and satisfaction. The individual can elect to share the mental state information. The mental state information is presented to the individual prior to the electing to share.

In the diagram 1300, the multiple mobile devices can be used singly or together to collect video data on a user 1310. While one person is shown, the video data can be collected on multiple people. A user 1310 can be observed as she or he is performing a task, experiencing an event, viewing a media presentation, and so on. The user 1310 can be shown one or more media presentations, political presentations, social media, or another form of displayed media. The one or more media presentations can be shown to a plurality of people. The media presentations can be displayed on an electronic display 1312 or another display. The data collected on the user 1310 or on a plurality of users can be in the form of one or more videos, video frames, still images, etc. The plurality of videos can be of people who are experiencing different situations. Some example situations can include the user or plurality of users being exposed to TV programs, movies, video clips, social media, and other such media. The situations could also include exposure to media such as advertisements, political messages, news programs, and so on. As noted before, video data can be collected on one or more users in substantially identical or different situations and viewing either a single media presentation or a plurality of presentations. The data collected on the user 1310 can be analyzed and viewed for a variety of purposes including expression analysis, mental state analysis, and so on. The electronic display 1312 can be on a laptop computer 1320 as shown, a tablet computer 1350, a computer enabled(smart) cell phone 1340, a television, a mobile monitor, or any other type of electronic device that includes computational power. In one embodiment, expression data is collected on a mobile device such as a smartphone 1340, a tablet computer 1350, a laptop computer 1320, or a watch 1370. Thus, the multiple sources can include at least one mobile device, such as a smartphone 1340 or a tablet 1350, or a wearable device such as a watch 1370 or glasses 1360 that are connected to a computing device. A mobile device can include a front-side camera and/or a back-side camera that can be used to collect expression data. Sources of expression data can include a webcam 1322, a phone camera 1342, a tablet camera 1352, a wearable camera 1362, and a mobile camera 1330. A wearable camera can comprise various camera devices, such as a watch camera 1372.

As the user 1310 is monitored, the user 1310 might move due to the nature of the task, boredom, discomfort, distractions, or for another reason. As the user moves, the camera with a view of the user's face can be changed. Thus, as an example, if the user 1310 is looking in a first direction, the line of sight 1324 from the webcam 1322 is able to observe the user's face, but if the user is looking in a second direction, the line of sight 1334 from the mobile camera 1330 is able to observe the user's face. Furthermore, in other embodiments, if the user is looking in a third direction, the line of sight 1344 from the phone camera 1342 is able to observe the user's face, and if the user is looking in a fourth direction, the line of sight 1354 from the tablet camera 1352 is able to observe the user's face. If the user is looking in a fifth direction, the line of sight 1364 from the wearable camera 1362, which can be a device such as the glasses 1360 shown and can be worn by another user or an observer, is able to observe the user's face. If the user is looking in a sixth direction, the line of sight 1374 from the wearable watch-type device 1370, with a camera 1372 included on the device, is able to observe the user's face. In other embodiments, the wearable device is another device, such as an earpiece with a camera, a helmet or hat with a camera, a clip-on camera attached to clothing, or any other type of wearable device with a camera or other sensor for collecting expression data. The user 1310 can also use a wearable device including a camera for gathering contextual information and/or collecting expression data on other users. Because the user 1310 can move her or his head, the facial data can be collected intermittently when she or he is looking in a direction of a camera. In some cases, multiple people can be included in the view from one or more cameras, and some embodiments include filtering out faces of one or more other people to determine whether the user 1310 is looking toward a camera. All or some of the expression data can be continuously or sporadically available from the various devices and other devices.

The captured video data can include facial expressions, and can be analyzed on a computing device such as the video capture device or on another separate device. The analysis can take place on one of the mobile devices discussed above, on a local server, on a remote server, and so on. In embodiments, some of the analysis takes place on the mobile device, while other analysis takes place on a server device. The analysis of the video data can include the use of a classifier. The video data can be captured using one of the mobile devices discussed above and sent to a server or another computing device for analysis. However, the captured video data including expressions can also be analyzed on the device which performed the capturing. The analysis can be performed on a mobile device where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device.

Figure 14:
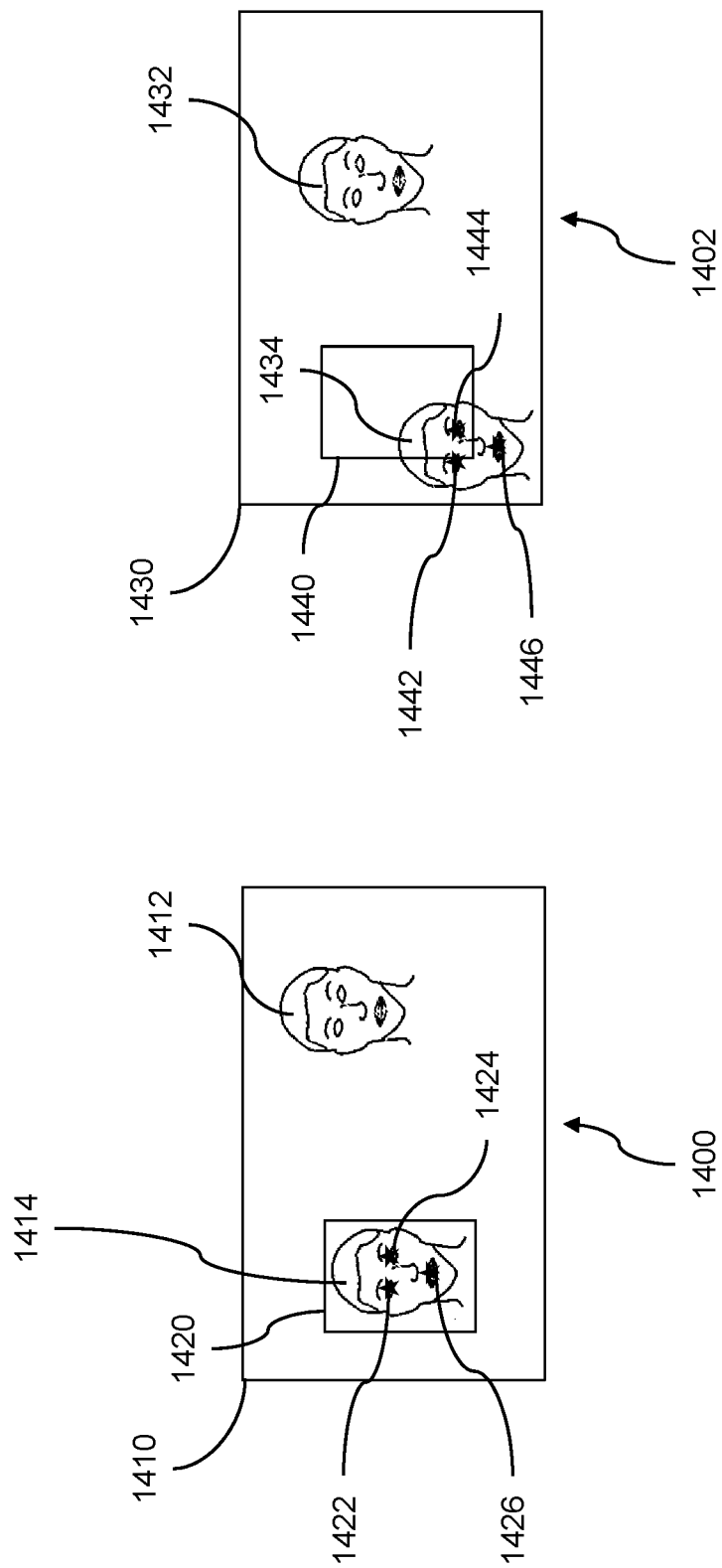
FIG. 14 illustrates feature extraction for multiple faces.

FIG. 14 illustrates feature extraction for multiple faces. Feature extraction for multiple faces can be used for sharing affect across a social network. Mental state data is collected from an individual. The mental state data is analyzed to produce mental state information. The mental state information is shared across a social network. The individual can elect to share the mental state information. The mental state information is presented to the individual prior to the electing. FIG. 14 illustrates feature extraction for multiple faces. The feature extraction for multiple faces can be performed for faces that can be detected in multiple images. The collected images can be analyzed for emotional metric generation. Image data, including facial images, is collected from a user interacting with a media presentation. Processors are used to analyze both the image data and the media presentation to extract emotional content. Emotional intensity metrics are determined and retained in a storage component. The emotional intensity metrics are coalesced into a summary intensity metric, which is displayed on a screen. The images can be collected from people as they interact with the Internet. In embodiments, the features of multiple faces are extracted for evaluating mental states. Features of a face or a plurality of faces can be extracted from collected video data. Feature extraction for multiple faces can be based on analyzing, using one or more processors, the mental state data for providing analysis of the mental state data to the individual. The feature extraction can be performed by analysis using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications, including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech, and handwriting recognition, and so on. Classification can be used for biometric identification of one or more people in one or more frames of one or more videos.

Returning to FIG. 14, the detection of the first face, the second face, and multiple faces can include identifying facial landmarks, generating a bounding box, and prediction of a bounding box and landmarks for a next frame, where the next frame can be one of a plurality of frames of a video containing faces. A first video frame 1400 includes a frame boundary 1410, a first face 1412, and a second face 1414. The video frame 1400 also includes a bounding box 1420. Facial landmarks can be generated for the first face 1412. Face detection can be performed to initialize a second set of locations for a second set of facial landmarks for a second face within the video. Facial landmarks in the video frame 1400 can include the facial landmarks 1422, 1424, and 1426. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. The estimating of a second rough bounding box can include the bounding box 1420. Bounding boxes can also be estimated for one or more other faces within the boundary 1410. The bounding box can be refined, as can one or more facial landmarks. The refining of the second set of locations for the second set of facial landmarks can be based on localized information around the second set of facial landmarks. The bounding box 1420 and the facial landmarks 1422, 1424, and 1426 can be used to estimate future locations for the second set of locations for the second set of facial landmarks in a future video frame from the first video frame.

A second video frame 1402 is also shown. The second video frame 1402 includes a frame boundary 1430, a first face 1432, and a second face 1434. The second video frame 1402 also includes a bounding box 1440 and the facial landmarks, or points, 1442, 1444, and 1446. In other embodiments, multiple facial landmarks are generated and used for facial tracking of the two or more faces of a video frame, such as the second shown video frame 1402. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, multiple facial points can be determined within a frame. One or more of the other facial points that are determined can correspond to a third face. The location of the bounding box 1440 can be estimated, where the estimating can be based on the location of the generated bounding box 1420 shown in the first video frame 1400. The three facial points shown, facial points, or landmarks, 1442, 1444, and 1446, might lie completely within the bounding box 1440 or might lie partially outside the bounding box 1440. For instance, the second face 1434 might have moved between the first video frame 1400 and the second video frame 1402. Based on the accuracy of the estimating of the bounding box 1440, a new estimation can be determined for a third, future frame from the video, and so on. The evaluation can be performed, all or in part, on semiconductor-based logic.

Figure 15:
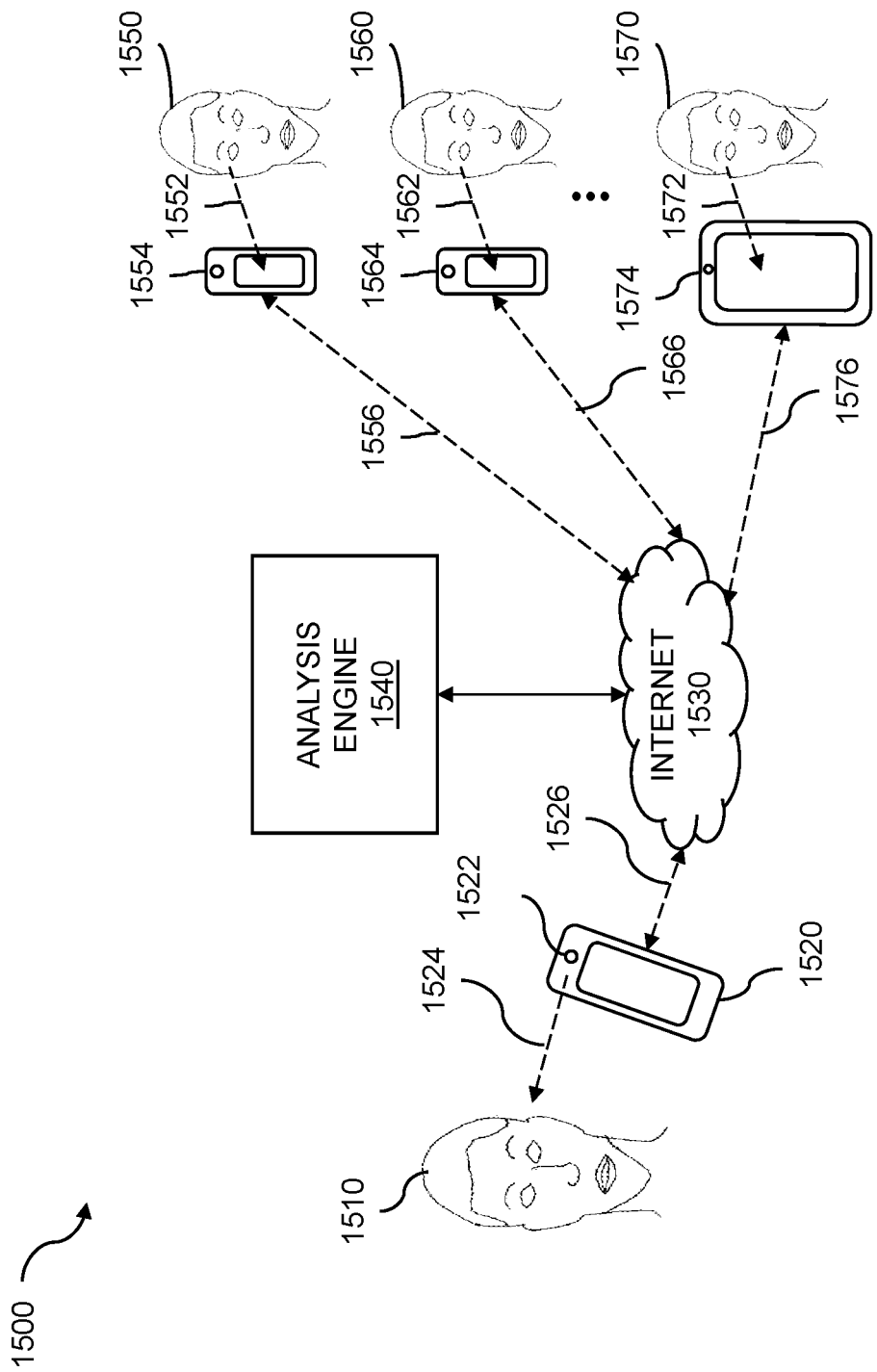
FIG. 15 shows live streaming of social video.

FIG. 15 shows live streaming of social video. Live streaming of social video can be used for sharing affect across a social network. Mental state data is collected from an individual. The mental state data can be collected over a period of time. The mental state data is analyzed to produce mental state information. The mental state information is shared across a social network. The mental state information that is shared can be a reflection of a mood for the individual. The mood can include one of a group including frustration, confusion, disappointment, hesitation, cognitive overload, focusing, being engaged, attending, boredom, exploration, confidence, trust, delight, and satisfaction. The individual can elect to share the mental state information. The mental state information is presented to the individual prior to the electing to share. The streaming and analysis can be facilitated by a video capture device, a local server, a remote server, a semiconductor-based logic, and so on. The streaming can be live streaming and can include mental state analysis, mental state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcasted as needed or when desirable. Examples of impromptu live stream videos can range from individuals simply wanting to share experiences with their social media followers, to live coverage of breaking news, emergencies, or natural disasters. The latter coverage is known as mobile journalism, or "mo jo", and is becoming increasingly common. With this type of coverage, news reporters can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscopes™ that can transmit a live recording from one user to that user's Periscopes™ account and other followers. The Periscopes™ app can be executed on a mobile device. The user's Periscopes™ followers can receive an alert whenever that user begins a video transmission. Another live-stream video platform is Twitch™ that can be used for video streaming of video gaming and broadcasts of various competitions and events.

The example 1500 shows a user 1510 broadcasting a video live stream to one or more people as shown by the person 1550, the person 1560, and the person 1570. A portable, network-enabled, electronic device 1520 can be coupled to a front-side camera 1522. The portable electronic device 1520 can be a smartphone, a PDA, a tablet, a laptop computer, and so on. The camera 1522 coupled to the device 1520 can have a line-of-sight view 1524 to the user 1510 and can capture video of the user 1510. The captured video can be sent to an analysis or recommendation engine 1540 using a network link 1526 to the Internet 1530. The network link can be a wireless link, a wired link, and so on. The recommendation engine 1540 can recommend to the user 1510 an app and/or platform that can be supported by the server and can be used to provide a video live stream to one or more followers of the user 1510. In the example 1500, the user 1510 has three followers: the person 1550, the person 1560, and the person 1570. Each follower has a line-of-sight view to a video screen on a portable, networked electronic device. In other embodiments, one or more followers follow the user 1510 using any other networked electronic device, including a computer. In the example 1500, the person 1550 has a line-of-sight view 1552 to the video screen of a device 1554; the person 1560 has a line-of-sight view 1562 to the video screen of a device 1564, and the person 1570 has a line-of-sight view 1572 to the video screen of a device 1574. The portable electronic devices 1554, 1564, and 1574 can each be a smartphone, a PDA, a tablet, and so on. Each portable device can receive the video stream being broadcasted by the user 1510 through the Internet 1530 using the app and/or platform that can be recommended by the recommendation engine 1540. The device 1554 can receive a video stream using the network link 1556, the device 1564 can receive a video stream using the network link 1566, the device 1574 can receive a video stream using the network link 1576, and so on. The network link can be a wireless link, a wired link, a hybrid link, and so on. Depending on the app and/or platform that can be recommended by the recommendation engine 1540, one or more followers, such as the persons, or followers, 1550, 1560, 1570, and so on, can reply to, comment on, and otherwise provide feedback to the user 1510 using their devices 1554, 1564, and 1574, respectively.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras connected to one or more computing devices for real-time or near-real-time processing. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from multiple viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include items such as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. These AUs can be used to recognize emotions experienced by the observed person. Emotion-related facial actions can be identified using the emotional facial action coding system (EMFACS) and the facial action coding system affect interpretation dictionary (FACSAID). For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness. The automated systems can be based on a probability estimate from one or more classifiers, where the probabilities can correlate with an intensity of an AU or an expression. The classifiers can be used to identify into which of a set of categories a given observation can be placed. In some cases, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from differences in illumination or shadowing changes between and among video frames. The HoG can be computed on the image or on an adjusted version of the image, where the adjustment of the image can include scaling, rotation, etc. The image can be adjusted by flipping the image around a vertical line through the middle of a face in the image. The symmetry plane of the image can be determined from the tracker points and landmarks of the image.

In embodiments, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor-based logic.

Figure 16:
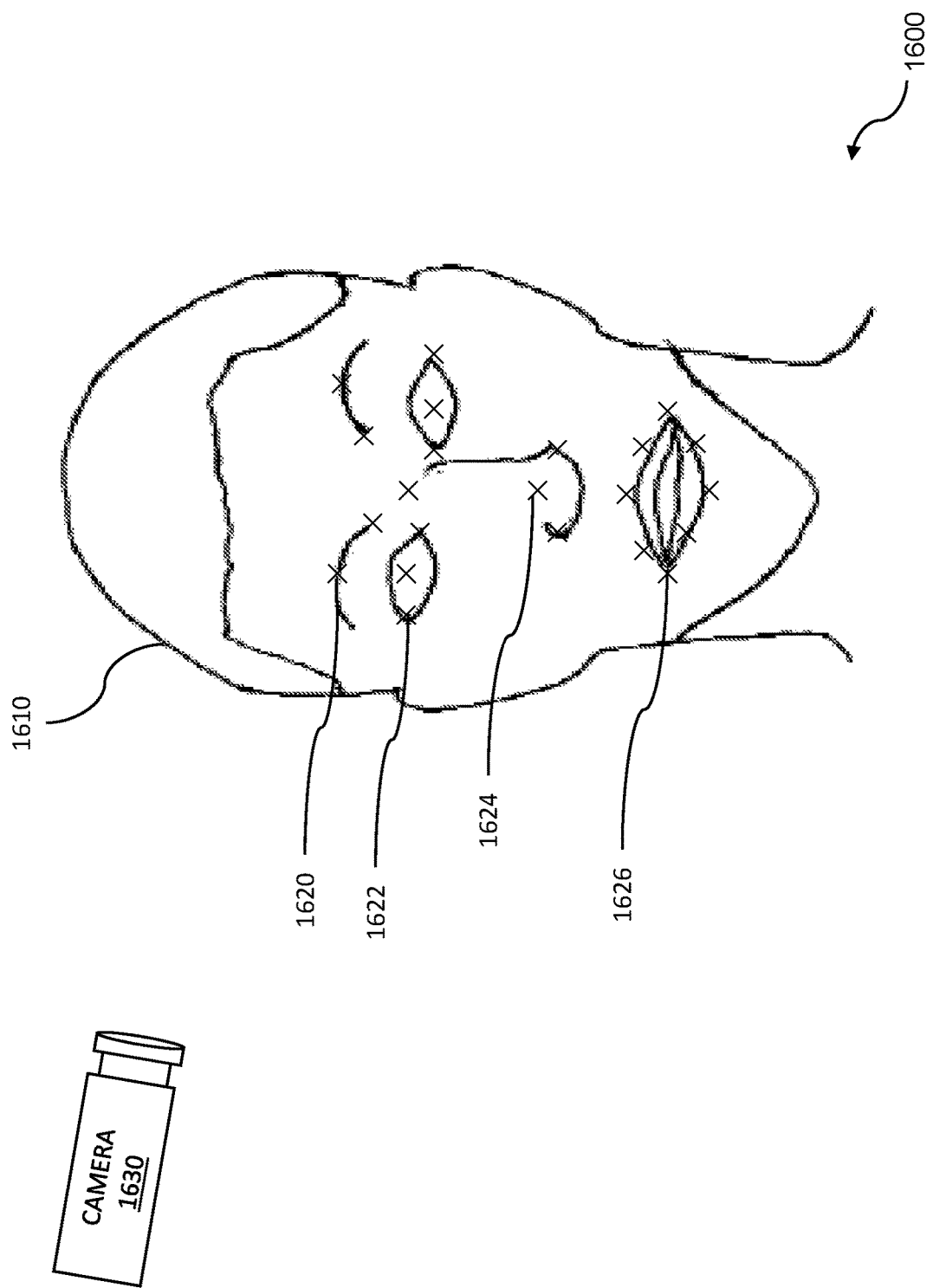
FIG. 16 shows example facial data collection including landmarks.

FIG. 16 shows example facial data collection including landmarks. Facial data including landmarks is collected for sharing affect across a social network. Mental state data is collected from an individual. The mental state data is analyzed to produce mental state information. The mental state information is shared across a social network. The individual can elect to share the mental state information. The mental state information is presented to the individual prior to the electing. In the example 1600, facial data including facial landmarks can be collected using a variety of electronic hardware and software techniques. The collecting of facial data including landmarks can be based on enabling an app by an individual. Image data, including facial images, is collected from a user interacting with a media presentation. Processors are used to analyze the image data and the media presentation to extract emotional content. Emotional intensity metrics are determined and retained in a storage component. The emotional intensity metrics are coalesced into a summary intensity metric, and the summary intensity metric is displayed on a screen. A face 1610 can be observed using a camera 1630 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a smartphone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 1630 relative to the face 1610, the number of cameras used, the illumination of the face, etc. In some cases, if the face 1610 is poorly lit or over-exposed (e.g. in an area of bright light), the processing of the facial data to identify facial landmarks might be rendered more difficult. In another example, the camera 1630 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 1620, an outer eye edge 1622, a nose 1624, a corner of a mouth 1626, and so on. Multiple facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Multiple action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 17:
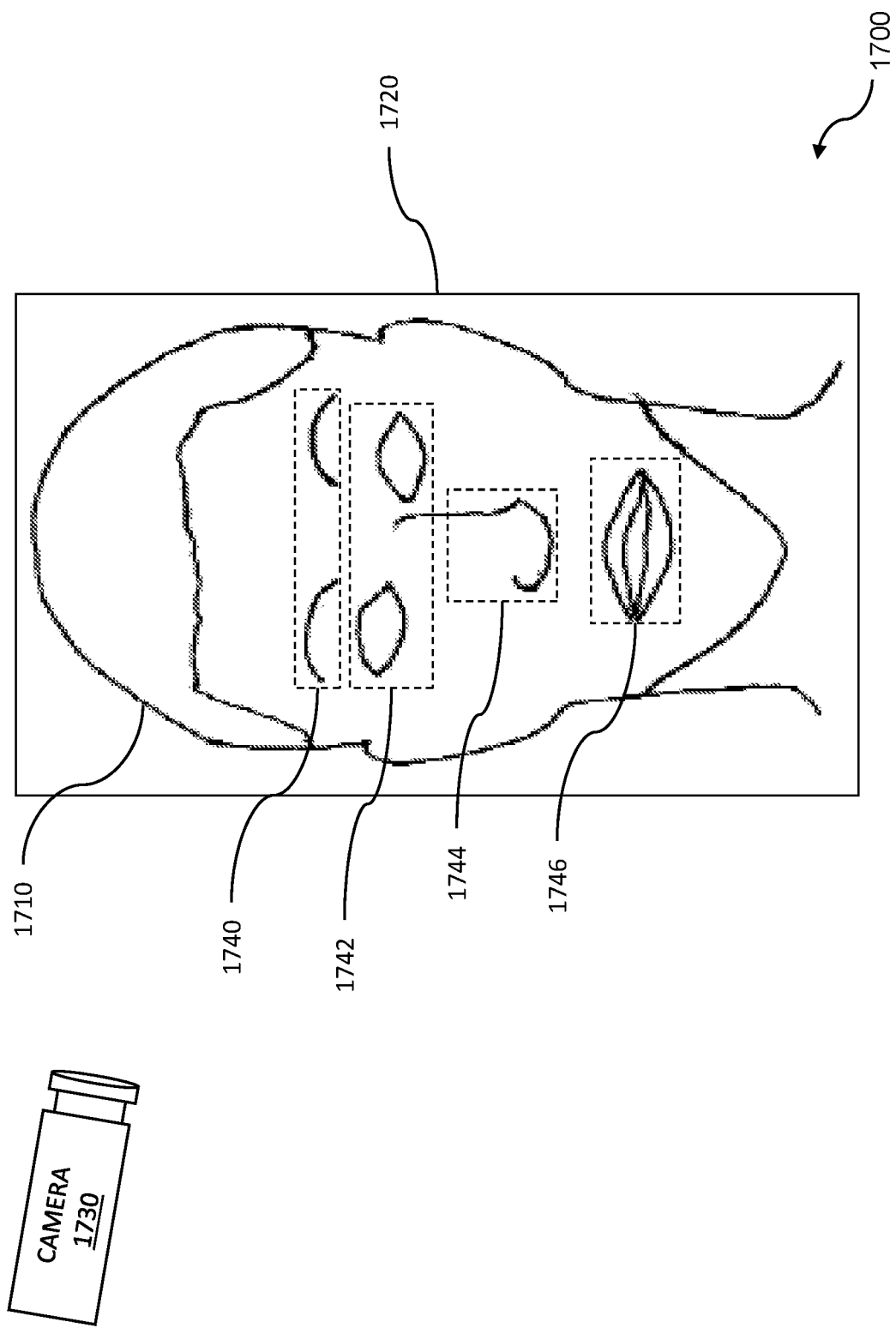
FIG. 17 shows example facial data collection including regions.

FIG. 17 shows example facial data collection including regions. The collected facial data including regions can be analyzed for sharing affect across a social network. Mental state data is collected from an individual. The mental state data can be collected over a period of time. The mental state data is analyzed to produce mental state information. The mental state information is shared across a social network. The mental state information that is shared can be a reflection of a mood for the individual. The mood can include one of a group including frustration, confusion, disappointment, hesitation, cognitive overload, focusing, being engaged, attending, boredom, exploration, confidence, trust, delight, and satisfaction. The individual can elect to share the mental state information. The mental state information is presented to the individual prior to the electing to share. The facial data including regions can be collected from people as they interact with the Internet. Various regions of a face can be identified and used for a variety of purposes including facial recognition, facial analysis, and so on. Facial analysis can be used to determine, predict, estimate, etc. mental states, emotions, and so on of a person from whom facial data can be collected. The one or more emotions that can be determined by the analysis can be represented by an image, a figure, an icon, etc. The representative icon can include an emoji. One or more emoji can be used to represent a mental state, a mood, etc. of an individual, to represent food, a geographic location, weather, and so on. The emoji can include a static image. The static image can be a predefined size such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1700, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1710 can be observed using a camera 1730, a sensor, a combination of cameras and/or sensors, and so on. The camera 1730 can be used to collect facial data that can be used to determine when a face is present in an image. When a face is present in an image, a bounding box 1720 can be placed around the face. Placement of the bounding box around the face can be based on detection of facial landmarks. The camera 1730 can be used to collect from the bounding box 1720 facial data, where the facial data can include facial regions. The facial data can be collected from a plurality of people using any of a variety of cameras. As previously discussed, the camera or cameras can include a webcam, where a webcam can include a video camera, a still camera, a thermal imager, a CCD device, a smartphone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1730 relative to the face 1710, the number of cameras and/or sensors used, the illumination of the face, any obstructions to viewing the face, and so on.

The facial regions that can be collected by the camera 1730, sensor, or combination of cameras and/or sensors can include any of a variety of facial features. The facial features that can be included in the facial regions that are collected can include eyebrows 1740, eyes 1742, a nose 1744, a mouth 1746, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include textures, gradients, colors, shapes, etc. The facial features can be used to determine demographic data, where the demographic data can include age, ethnicity, culture, gender, etc. Multiple textures, gradients, colors, shapes, and so on, can be detected by the camera 1730, sensor, or combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, wrinkles, and so on. Another texture that can be used to evaluate a facial region can include a smooth portion of skin such as a smooth portion of a cheek. A gradient in a facial region can include values assigned to local skin texture, shading, etc. A gradient can be used to encode, for example, a texture, by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, gender, etc. A shape in a facial region can include shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be included in the image can include one or more faces. A boundary can refer to a contour in an image plane where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change, in color, brightness, etc. within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, edges, etc. Any classifier can be used for the analysis, including, but not limited to, density estimation, support vector machines (SVM), logistic regression, classification trees, and so on. By way of example, consider facial features that can include the eyebrows 1740. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate the person from whom the facial data can be collected is annoyed, confused, unhappy, and so on. In another example, consider facial features that can include a mouth 1746. One or more classifiers can be used to analyze the facial region that can include the mouth to determine a probability for either a presence or an absence of mouth edges turned up to form a smile. Multiple classifiers can be used to determine one or more facial expressions.

Figure 18:
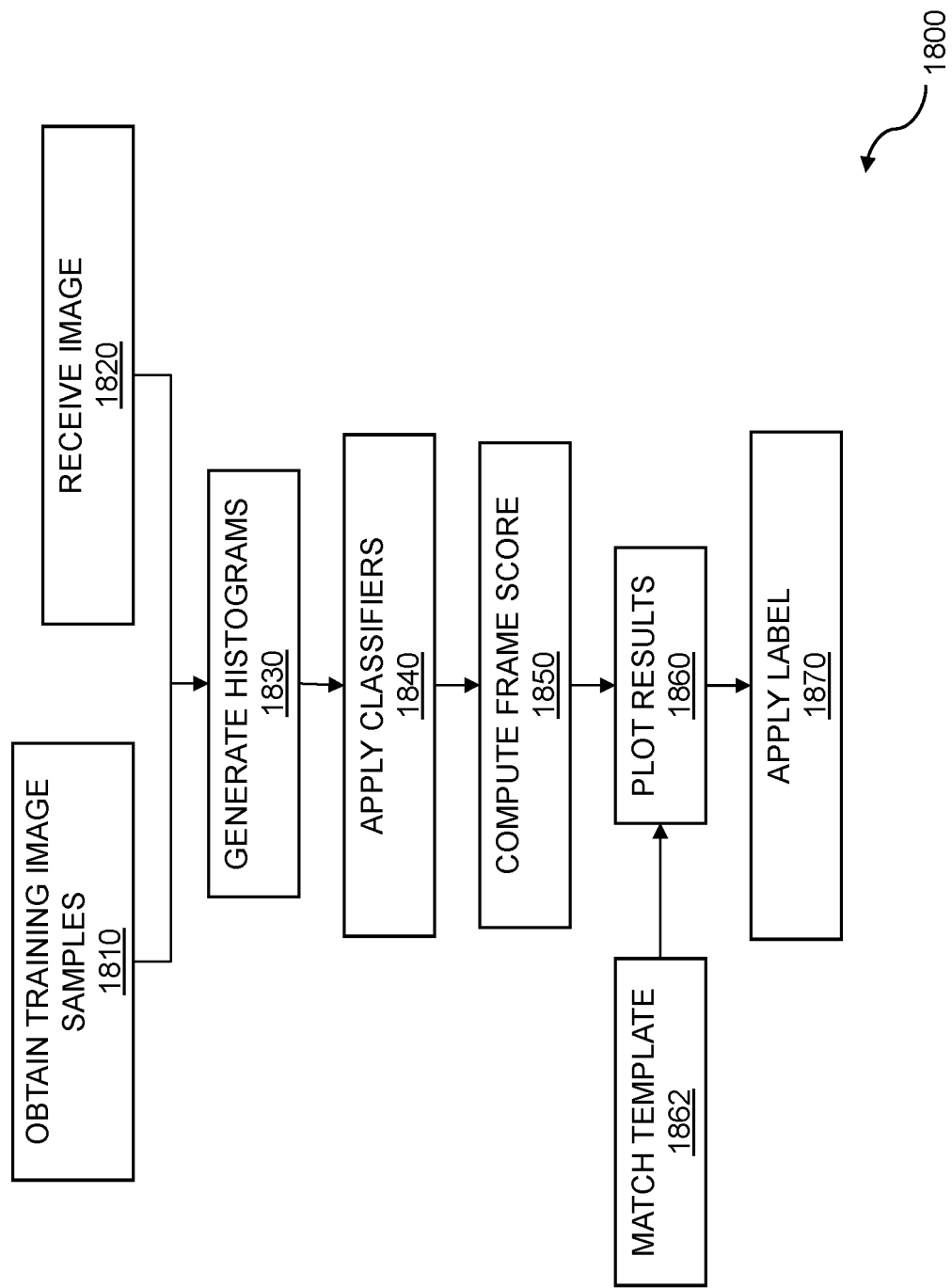
FIG. 18 is a flow diagram for detecting facial expressions.

FIG. 18 is a flow diagram for detecting facial expressions. Detection of facial expressions can be used for sharing affect across a social network. Images can be collected for sharing affect across a social network. Mental state data is collected from an individual. The mental state data is analyzed to produce mental state information. The mental state information is shared across a social network. The individual can elect to share the mental state information. The mental state information is presented to the individual prior to the electing. The flow 1800, or portions thereof, can be implemented in semiconductor logic, can be accomplished using a mobile device, can be accomplished using a server device, and so on. The flow 1800 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1800 begins by obtaining training image samples 1810. The image samples can include a plurality of images of one or more people. Human coders who are trained to correctly identify AU codes based on the FACS can code the images. The training, or "known good," images can be used as a basis for training a machine learning technique. Once trained, the machine learning technique can be used to identify AUs in other images that can be collected using a camera, a sensor, and so on. The flow 1800 continues with receiving an image 1820. The image 1820 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1800 continues with generating histograms 1830 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1800 continues with applying classifiers 1840 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1800 continues with computing a frame score 1850. The score computed for an image, where the image can be a frame from a video, can be used to determine the presence of a facial expression in the image or video frame. The score can be based on one or more versions of the image 1820 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1800 continues with plotting results 1860. The results that are plotted can include one or more scores for one or more frames computed over a given time t. For example, the plotted results can include classifier probability results from analysis of HoGs for a sequence of images and video frames. The plotted results can be matched with a template 1862. The template can be temporal and can be represented by a centered box function or another function. A best fit with one or more templates can be found by computing a minimum error. Other best-fit techniques can include polynomial curve fitting, geometric curve fitting, and so on. The flow 1800 continues with applying a label 1870. The label can be used to indicate that a particular facial expression has been detected in the one or more images or video frames which constitute the image 1820 that was received. The label can be used to indicate that any of a range of facial expressions has been detected, including a smile, an asymmetric smile, a frown, and so on. Various steps in the flow 1800 may be changed in order, repeated, omitted, or the like without departing from the disclosed concepts. Various embodiments of the flow 1800 can be included in a computer program product embodied in a non-transitory computer readable medium that includes code executable by one or more processors. Various embodiments of the flow 1800, or portions thereof, can be included on a semiconductor chip and implemented in special purpose logic, programmable logic, and so on.

Figure 19:
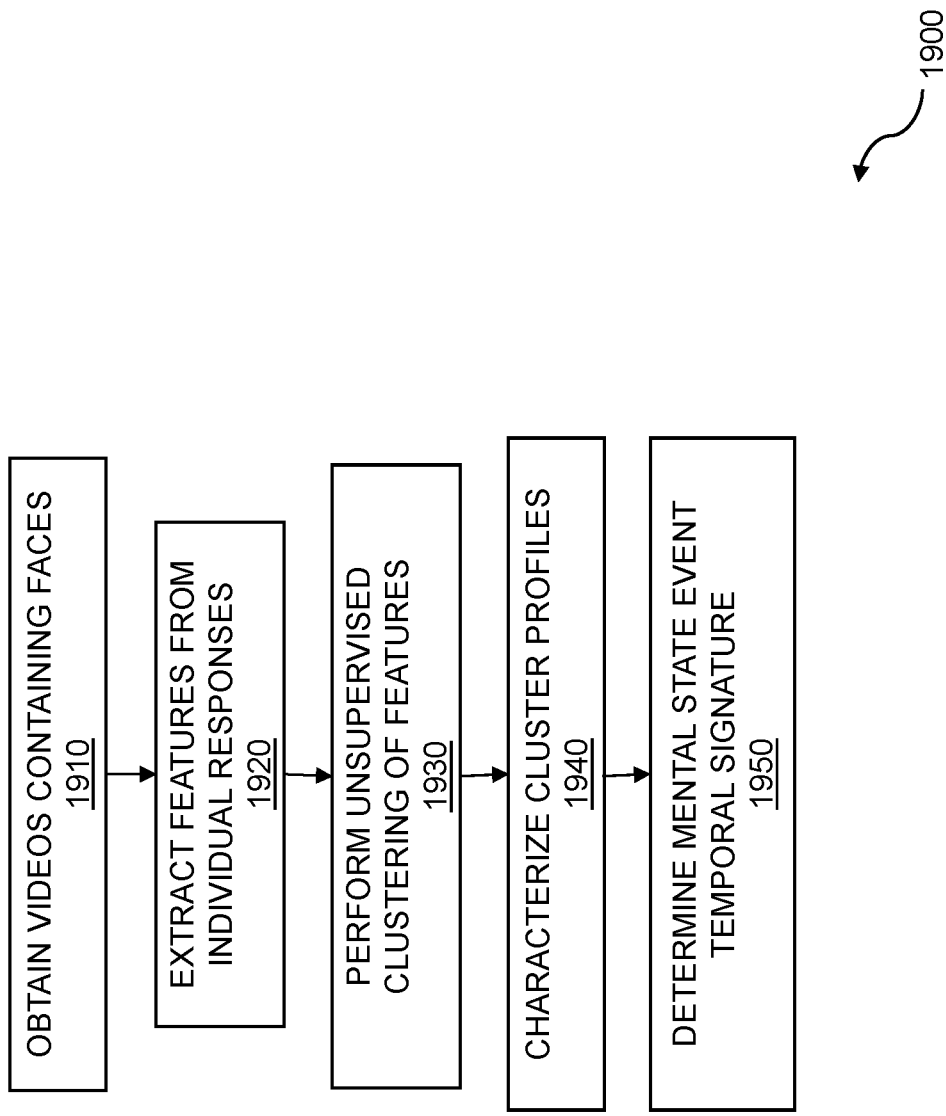
FIG. 19 is a flow diagram for large-scale clustering of facial events.

FIG. 19 is a flow diagram for large-scale clustering of facial events. Large-scale clustering of facial events can be used for sharing affect across a social network. Mental state data is collected from an individual. The mental state data can be collected over a period of time. The mental state data is analyzed to produce mental state information. The mental state information is shared across a social network. The mental state information that is shared can be a reflection of a mood for the individual. The mood can include one of a group including frustration, confusion, disappointment, hesitation, cognitive overload, focusing, being engaged, attending, boredom, exploration, confidence, trust, delight, and satisfaction. The individual can elect to share the mental state information. The mental state information is presented to the individual prior to the electing to share. The large-scale clustering of facial events can be performed for data collected from a remote computing device. The facial events can be collected from people as they interact with the Internet. The clustering and evaluation of facial events can be augmented using a mobile device, a server, semiconductor-based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1900 includes obtaining videos containing faces 1910. The videos can be obtained using one or more cameras, where the cameras can include a webcam coupled to one or more devices employed by the one or more people using the web-based framework. The flow 1900 continues with extracting features from the individual responses 1920. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1900 continues with performing unsupervised clustering of features 1930. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1900 includes characterizing cluster profiles 1940. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. The number of smiles resulting from people viewing a humorous video can be compared to various demographic groups, where the groups can be formed based on geographic location, age, ethnicity, gender, and so on.

The flow 1900 can include determining mental state event temporal signatures 1950. The mental state event temporal signatures can include information on rise time to facial expression intensity, fall time from facial expression intensity, duration of a facial expression, and so on. In some embodiments, the mental state event temporal signatures are associated with certain demographics, ethnicities, cultures, etc. The mental state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. Various steps in the flow 1900 may be changed in order, repeated, omitted, or the like without departing from the disclosed concepts. Various embodiments of the flow 1900 can be included in a computer program product embodied in a non-transitory computer readable medium that includes code executable by one or more processors. Various embodiments of the flow 1900, or portions thereof, can be included on a semiconductor chip and implemented in special purpose logic, programmable logic, and so on.

Figure 20:
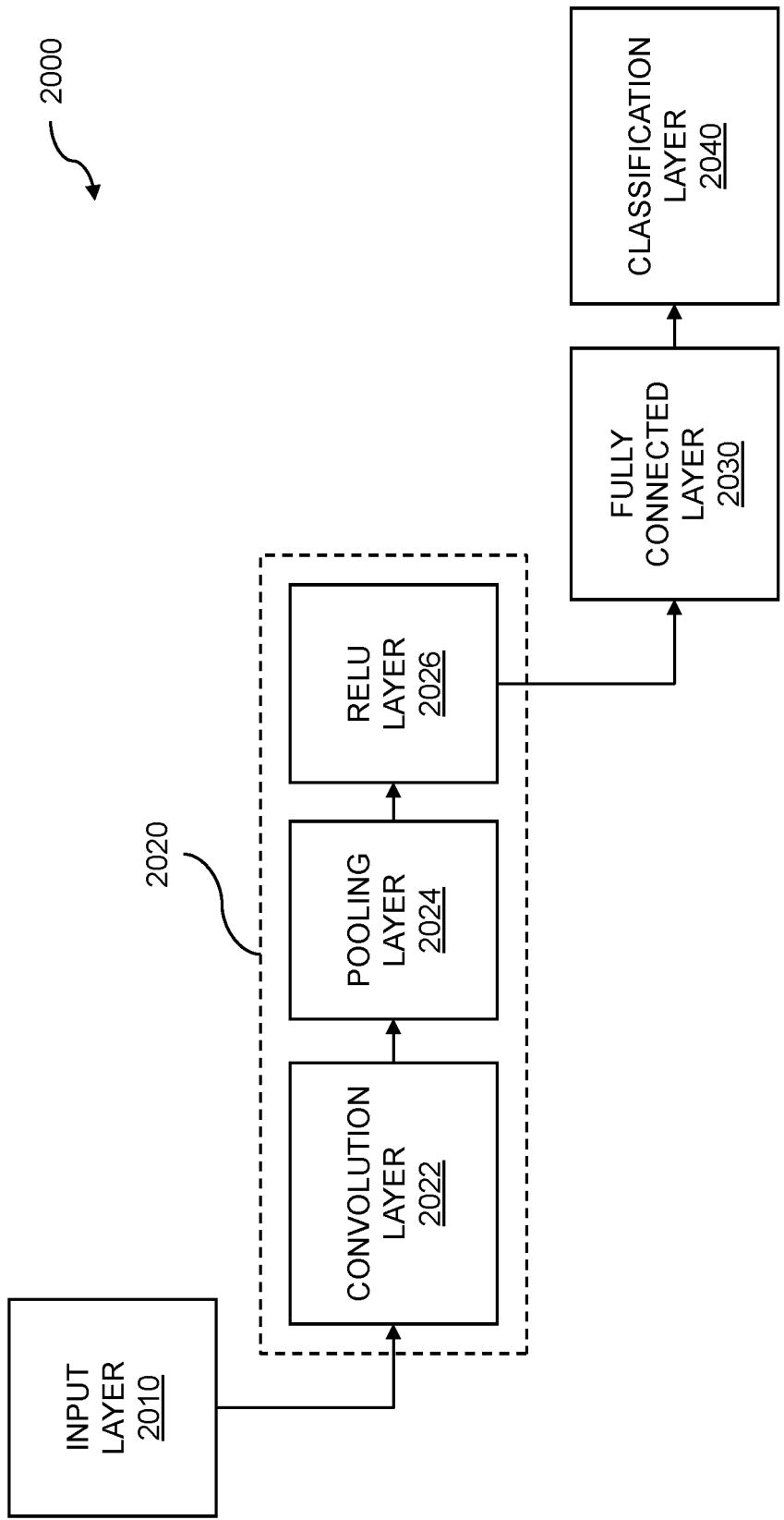
FIG. 20 illustrates a system diagram for deep learning for emotion analysis.

FIG. 20 illustrates a system diagram for deep learning for emotion analysis. Sharing affect across a social network can be based on deep learning for emotion analysis. Mental state data is collected from an individual. The mental state data is analyzed to produce mental state information. The mental state information is shared across a social network. The individual can elect to share the mental state information. The mental state information is presented to the individual prior to the electing. Emotion analysis is a very complex task. Understanding and evaluating moods, emotions, or mental states requires a nuanced evaluation of facial expressions or other cues generated by people. Mental state analysis is important in many areas such as research, psychology, business, intelligence, law enforcement, and so on. The understanding of mental states can be used in a variety of fields, such as improving marketing analysis, assessing the effectiveness of customer service interactions and retail experiences, and evaluating the consumption of content such as movies and videos. Identifying points of frustration in a customer transaction can allow a company to take action to address the causes of the frustration. By streamlining processes, key performance areas such as customer satisfaction and customer transaction throughput can be improved, resulting in increased sales and revenues. In a content scenario, producing compelling content that achieves the desired effect (e.g. fear, shock, laughter, etc.) can result in increased ticket sales and/or increased advertising revenue. If a movie studio is producing a horror movie, it is desirable to know if the scary scenes in the movie are achieving the desired effect. By conducting tests in sample audiences, and analyzing faces in the audience, a computer-implemented method and system can process thousands of faces to assess the mental state at the time of the scary scenes. In many ways, such an analysis can be more effective than surveys that ask audience members questions, since audience members may consciously or subconsciously change answers based on peer pressure or other factors. However, spontaneous facial expressions can be more difficult to conceal. Thus, by analyzing facial expressions en masse in real time, important information regarding the mental state of the audience can be obtained.

Analysis of facial expressions is also a complex undertaking. Image data, where the image data can include facial data, can be analyzed to identify a range of facial expressions. The facial expressions can include a smile, frown, smirk, and so on. The image data and facial data can be processed to identify the facial expressions. The processing can include analysis of expression data, action units, gestures, mental states, physiological data, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, and can include a head tilt to the side, a forward lean, a smile, a frown, as well as many other gestures. Other types of data including the physiological data can be obtained, where the physiological data can be obtained using a camera or other image capture device, without contacting the person or persons. Respiration, heart rate, heart rate variability, perspiration, temperature, and other physiological indicators of mental state can be determined by analyzing the images and video data.

Deep learning is a branch of machine learning which seeks to imitate in software the activity which takes place in layers of neurons in the neocortex of the human brain. This imitative activity can enable software to "learn" to recognize and identify patterns in data, where the data can include digital forms of images, sounds, and so on. The deep learning software is used to simulate the large array of neurons of the neocortex. This simulated neocortex, or artificial neural network, can be implemented using mathematical formulas that are evaluated on processors. With the ever-increasing capabilities of the processors, increasing numbers of layers of the artificial neural network can be processed.

Deep learning applications include processing of image data, audio data, and so on. Image data applications include image recognition, facial recognition, etc. Image data applications can include differentiating dogs from cats, identifying different human faces, and the like. The image data applications can include identifying moods, mental states, emotional states, and so on, from the facial expressions of the faces that are identified. Audio data applications can include analyzing audio such as ambient room sounds, physiological sounds such as breathing or coughing, noises made by an individual such as tapping and drumming, voices, and so on. The voice data applications can include analyzing a voice for timbre, prosody, vocal register, vocal resonance, pitch, loudness, speech rate, or language content. The voice data analysis can be used to determine one or more moods, mental states, emotional states, etc.

The artificial neural network (ANN) which forms the basis for deep learning is based on layers. The layers can include an input layer, a convolution layer, a fully connected layer, a classification layer, and so on. The input layer can receive input data such as image data, where the image data can include a variety of formats including pixel formats. The input layer can then perform processing such as identifying boundaries of the face, identifying landmarks of the face, extracting features of the face, and/or rotating a face within the plurality of images. The convolution layer can represent an artificial neural network such as a convolutional neural network. A convolutional neural network (CNN) can contain a plurality of hidden layers within it. A convolutional layer can reduce the amount of data feeding into a fully connected layer. The fully connected layer processes each pixel/data point from the convolutional layer. A last layer within the multiple layers can provide output indicative of mental state. The last layer of the convolutional neural network can be the final classification layer. The output of the final classification layer can be indicative of the mental states of faces within the images that are provided to the input layer.

Deep networks including deep convolutional neural networks can be used for facial expression parsing. A first layer of the deep network includes multiple nodes, where each node represents a neuron within a neural network. The first layer can receive data from an input layer. The output of the first layer can feed to a second layer, where the latter layer also includes multiple nodes. A weight can be used to adjust the output of the first layer which is being input to the second layer. Some layers in the convolutional neural network can be hidden layers. The output of the second layer can feed to a third layer. The third layer can also include multiple nodes. A weight can adjust the output of the second layer which is being input to the third layer. The third layer may be a hidden layer. Outputs of a given layer can be feed to next layer. Weights adjust the output of one layer as it is feed to the next layer. When the final layer is reached, the output of the final layer can be a facial expression, a mental state, a characteristic of a voice, and so on. The facial expression can be identified using a hidden layer from the one or more hidden layers. The weights can be provided on inputs to the multiple layers to emphasize certain facial features within the face. The convolutional neural network can be trained to identify facial expressions, voice characteristics, etc. The training can include assigning weights to inputs on one or more layers within the multilayered analysis engine. One or more of the weights can be adjusted or updated during training. The assigning weights can be accomplished during a feed-forward pass through the multilayered neural network. In a feed-forward arrangement, the information moves forward, from the input nodes, through the hidden nodes and on to the output nodes. Additionally, the weights can be updated during a backpropagation process through the multilayered analysis engine.

Returning to the figure, FIG. 20 illustrates a system diagram 2000 for deep learning. The system deep learning can be accomplished using a convolution neural network or other techniques. The deep learning can accomplish facial recognition and analysis tasks. The network includes an input layer 2010. The input layer 2010 receives image data. The image data can be input in a variety of formats, such as JPEG, TIFF, BMP, and GIF. Compressed image formats can be decompressed into arrays of pixels, wherein each pixel can include an RGB tuple. The input layer 2010 can then perform processing such as identifying boundaries of the face, identifying landmarks of the face, extracting features of the face, and/or rotating a face within the plurality of images.

The network includes a collection of intermediate layers 2020. The multilayered analysis engine can include a convolutional neural network. Thus, the intermediate layers can include a convolution layer 2022. The convolution layer 2022 can include multiple sublayers, including hidden layers within it. The output of the convolution layer 2022 feeds into a pooling layer 2024. The pooling layer 2024 performs a data reduction, which makes the overall computation more efficient. Thus, the pooling layer reduces the spatial size of the image representation to reduce the number of parameters and computation in the network. In some embodiments, the pooling layer is implemented using filters of size 2×2, applied with a stride of two samples for every depth slice along both width and height, resulting in a reduction of 75-percent of the downstream node activations. The multilayered analysis engine can further include a pooling layer 2024 that is a max pooling layer. Thus, in embodiments, the pooling layer is a max pooling layer, in which the output of the filters is based on a maximum of the inputs. For example, with a 2×2 filter, the output is based on a maximum value from the four input values. In other embodiments, the pooling layer is an average pooling layer or L2-norm pooling layer. Various other pooling schemes are possible.

The intermediate layers can include a Rectified Linear Units (RELU) layer 2026. The output of the pooling layer 2024 can be input to the RELU layer 2026. In embodiments, the RELU layer implements an activation function such as $f(x)-max(0, x)$, thus providing an activation with a threshold at zero. In some embodiments, the RELU layer 2026 is a leaky RELU layer. In this case, instead of the activation function providing zero when x<0, a small negative slope is used, resulting in an activation function such as $f(x)=1(x<0)(\alpha x)+1(x>=0)(x)$. This can reduce the risk of "dying RELU" syndrome, where portions of the network can be "dead" with nodes/neurons that do not activate across the training dataset. The image analysis can comprise training a multilayered analysis engine using the plurality of images, wherein the multilayered analysis engine can include multiple layers that include one or more convolutional layers 2022 and one or more hidden layers, and wherein the multilayered analysis engine can be used for emotional analysis.

The example 2000 includes a fully connected layer 2030. The fully connected layer 2030 processes each pixel/data point from the output of the collection of intermediate layers 2020. The fully connected layer 2030 takes all neurons in the previous layer and connects them to every single neuron it has. The output of the fully connected layer 2030 provides input to a classification layer 2040. The output of the classification layer 2040 provides a facial expression and/or mental state as its output. Thus, a multilayered analysis engine such as the one depicted in FIG. 20 processes image data using weights, models the way the human visual cortex performs object recognition and learning, and is effective for analysis of image data to infer facial expressions and mental states.

Figure 21:
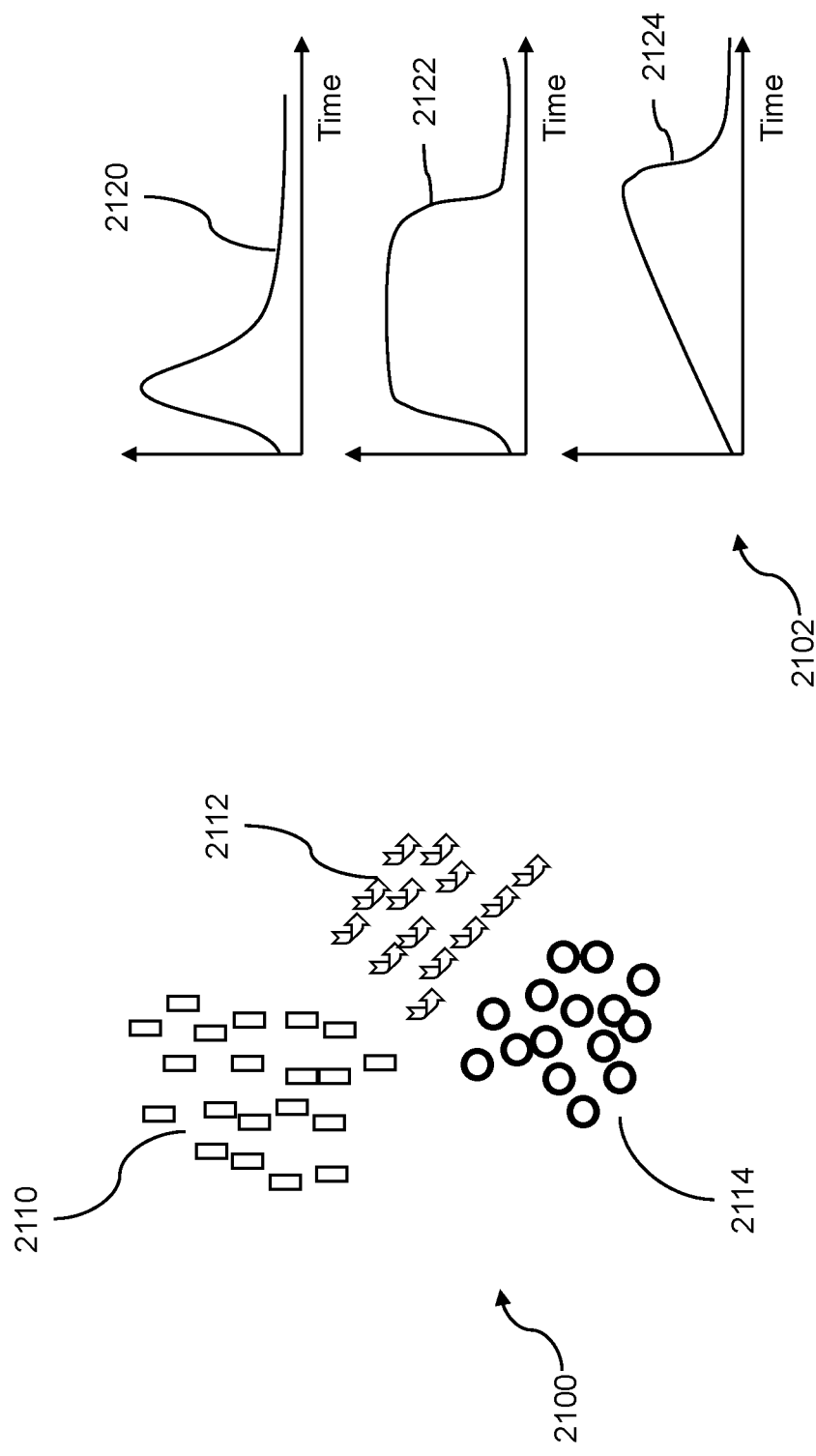
FIG. 21 shows unsupervised clustering of features and characterizations of cluster profiles.

FIG. 21 shows unsupervised clustering of features and characterizations of cluster profiles. Unsupervised clustering of features and characteristics of cluster profiles can be performed for sharing affect across a social network. Mental state data is collected from an individual. The mental state data can be collected over a period of time. The mental state data is analyzed using processors to produce mental state information. The mental state information is shared across a social network. The mental state information that is shared can be a reflection of a mood for the individual. The mood can include one of a group including frustration, confusion, disappointment, hesitation, cognitive overload, focusing, being engaged, attending, boredom, exploration, confidence, trust, delight, and satisfaction. The individual can elect to share the mental state information. The mental state information is presented to the individual prior to the electing to share. Features including samples of facial data can be clustered using unsupervised clustering. Various clusters can be formed which include similar groupings of facial data observations. The example 2100 shows three clusters, clusters 2110, 2112, and 2114. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 2102 can be generated based on the clusters that can be formed from unsupervised clustering, with time shown on the x-axis and intensity or frequency shown on the y-axis. The cluster profiles can be based on captured facial data, including facial expressions. The cluster profile 2120 can be based on the cluster 2110, the cluster profile 2122 can be based on the cluster 2112, and the cluster profile 2124 can be based on the cluster 2114. The cluster profiles 2120, 2122, and 2124 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 22A:
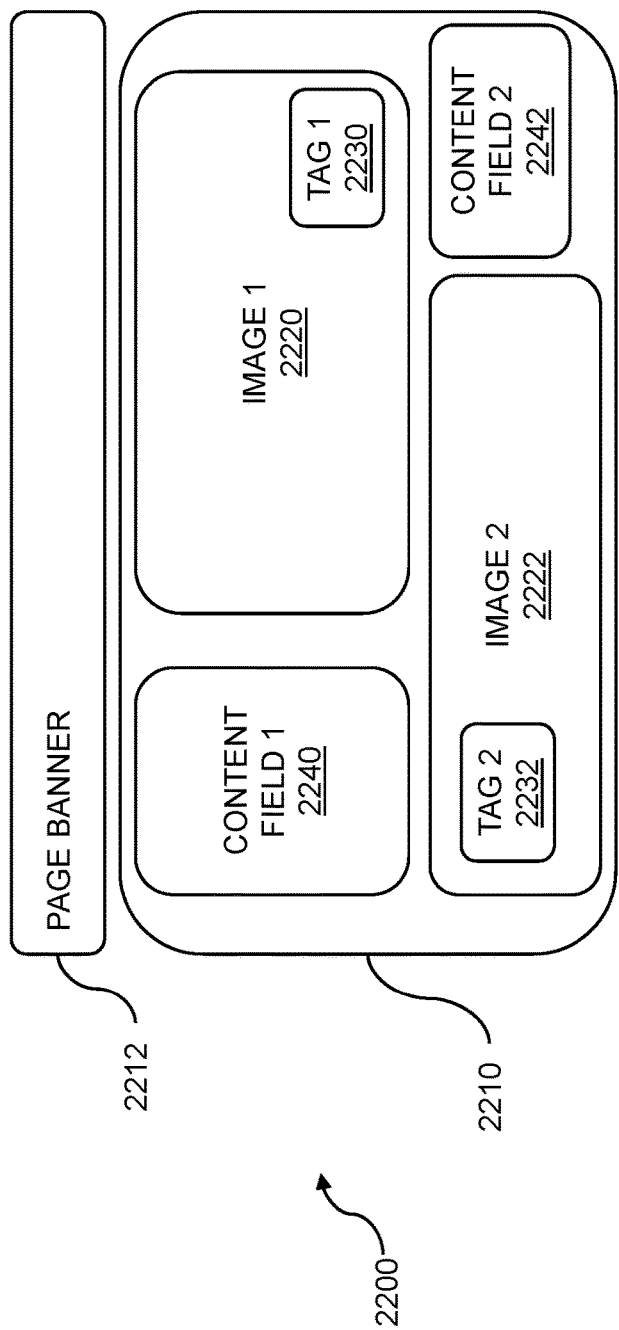
FIG. 22A shows example tags embedded in a webpage.

FIG. 22A shows example tags embedded in a webpage. Tags can be embedded in a webpage and can be used for sharing affect across a social network. Mental state data is collected from an individual. The mental state data is analyzed to produce mental state information. The mental state information is shared across a social network. The individual can elect to share the mental state information. The mental state information is presented to the individual prior to the electing. Once a tag is detected, a mobile device, a server, semiconductor-based logic, etc. can be used to evaluate associated facial expressions. A webpage 2200 can include a page body 2210, a page banner 2212, and so on. The page body can include one or more objects, where the objects can include text, images, videos, audio, and so on. The example page body 2210 shown includes a first image, image 1 2220; a second image, image 2 2222; a first content field, content field 1 2240; and a second content field, content field 2 2242. In practice, the page body 2210 can contain multiple images and content fields and can include one or more videos, one or more audio presentations, and so on. The page body can include embedded tags, such as tag 1 2230 and tag 2 2232. In the example shown, tag 1 2230 is embedded in image 1 2220, and tag 2 2232 is embedded in image 2 2222. In embodiments, multiple tags are imbedded. Tags can also be imbedded in content fields, in videos, in audio presentations, etc. When a user mouses over a tag or clicks on an object associated with a tag, the tag can be invoked. For example, when the user mouses over tag 1 2230, tag 1 2230 can then be invoked. Invoking tag 1 2230 can include enabling a camera coupled to a user's device and capturing one or more images of the user as the user views a media presentation (or digital experience). In a similar manner, when the user mouses over tag 2 2232, tag 2 2232 can be invoked. Invoking tag 2 2232 can also include enabling the camera and capturing images of the user. In other embodiments, other actions are taken based on invocation of the one or more tags. Invoking an embedded tag can initiate an analysis technique, post to social media, award the user a coupon or another prize, initiate mental state analysis, perform emotion analysis, and so on.

Figure 22B:
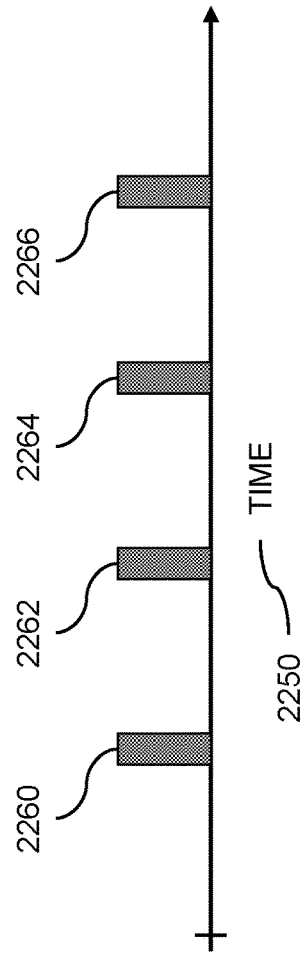
FIG. 22B shows invoking tags to collect images.

FIG. 22B shows invoking tags to collect images. The invoking tags to collect images can be used for sharing affect across a social network. The invoking tags to collect images can be used for people as they interact with various content provided to them, including content provided over the Internet. The tags can be related to analysis of mental state data for an individual. A mood dashboard can be displayed to the individual based on the analyzing. As previously stated, a media presentation can be a video, a webpage, and so on. A video 2202 can include one or more embedded tags, such as a tag 2260, another tag 2262, a third tag 2264, a fourth tag 2266, and so on. In practice, multiple tags can be included in the media presentation. The one or more tags can be invoked during the media presentation. The collection of the invoked tags can occur over time, as represented by a timeline 2250. When a tag is encountered in the media presentation, the tag can be invoked. When the tag 2260 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 2260 does not enable the camera nor capture images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages, advertising messages, social media sharing, etc. and that enable the camera and image capture when invoked would be embedded in the media presentation social media sharing, and so on. However, tags imbedded in the media presentation that are related to advertisements would not enable the camera when invoked. Various other situations of tag invocation are possible.

The capturing of images, videos, frames from video, etc. of one or more individuals results in substantial quantities of data that is stored for analysis, evaluation, comparison, aggregation, and other purposes. The image and video quality can vary depending on the capabilities of the machine or electronic device that is gathering the image and video data. The video framerate can include 15 frames per second (fps), 30 fps, and so on. The data that is received by the one or more individuals, such as content provided by a content provider and delivered over the Internet from a website rendered for the one or more individuals, can also be stored. Further, key clicks, mouse clicks, invoking tags, and other directed and automatic user actions result in additional data. The result of the capturing of video data, content, user web journey information, and so on is that the volume of data increases over time.

The data, such as the video data collected from an individual, includes mental state data, facial data, and so on. The mental state data from the one or more individuals can be analyzed to determine one or more moods, one or more mental states, one or more emotional states, etc., for the one or more individuals. The purposes of the analysis can vary and can include determining whether a website, web content, and so on makes a given individual happy, sad, angry, and so on. Such analysis can compare recently collected data to data collected in the past, where the past can be earlier in the day, a previous day, an earlier week, last year, etc. This "data telescoping" can be useful to both the individual consumer of web content and to the content provider of the web and other content. The data telescoping can be used to recommend and/or direct an individual to a website that makes her or him happy, to avoid web sites that induce anger, and so on. Additionally, the data telescoping can be used by a content provider to send to an individual content in which that individual is interested, to not send content that makes the individual angry, etc.

The value of the stored data changes over time. Current data can have the highest value and relevance, and can be stored in its entirety at a micro level. As the data ages, the typical trend is for the data to become less useful for such actions as predicting a current mental or emotional state in an individual, determining which content to provide, and so on. Various techniques can be used to determine what to do with the aging data. For example, after a week, the mental state data for an individual may be less relevant for determining current mental or emotional state, but can still maintain relevance for making comparisons of moods, emotions, mental states, determining trends, and so on. Over time, the data can be aggregated to time intervals. Such time intervals can include aggregating to one second intervals after a week, aggregating to the minute after a month, aggregating to an hour after a year, etc. The aggregation of data can be based on different techniques. One technique for data aggregation can include overall levels identified in the data such as whether the individual is happier, angrier, more confused, etc., when visiting a website or other content conduit. Another technique for data aggregation can include events such as numbers of smiles, eyebrow raises, scowls, etc. Aggregation of the data can also be based on filters used to identify data that should be kept, and other data that should be discarded.

The techniques used for the storage of the data are based on cost of storage, convenience of storage, uses of the data, and so on. Such data "warehousing" typically supports multiple uses of the data. A content provider may want to know the current mental and emotional states of an individual in order to provide that individual with content that will make that individual happy. The data storage accessed by the content provider would be fast and "nearby" for ready access, right now. By comparison, data scientists studying the collected data may be content with slower, "farther away" storage. This latter class of storage provides for inexpensive storage of larger quantities of data than does the former class of storage.

Figure 23A:
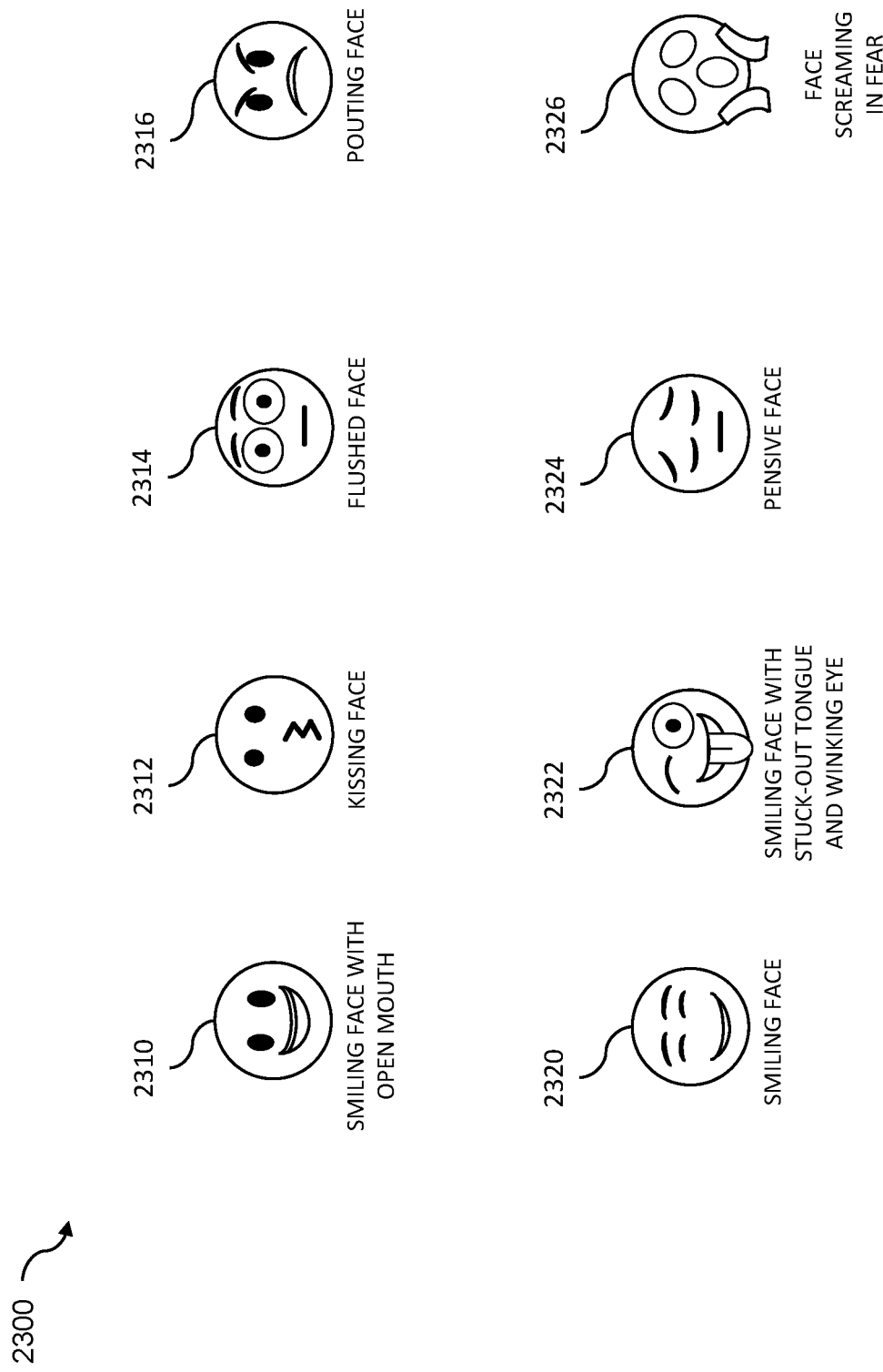
FIG. 23A shows example emoji.

FIG. 23A shows example emoji 2300. Emoji such as those seen in the example have come in to widespread use in a variety of electronic and other communications that can include email, text messages (SMS), social networking apps, and so on. Emoji can denote geographic locations, types of weather, pets and other animals, various objects, facial expressions, etc. Emoji can be specific to a variety of activities, applications, business practices, cultural norms, foods, and so on. The example emoji 2300 illustrate a variety of facial expressions. The facial expressions can imply one or more mental states, one or more moods, etc. The emoji for facial expressions can include a smiling face with open mouth, a white smiling face (sometimes referred to as the generic smiley face), a winking face, a kissing face with closed eyes, a kissing face, a face with stuck out tongue and winking, a face with stuck out tongue, a face with stuck out tongue and tightly closed eyes, a flushed face, a pensive face, a disappointed face, an unamused face, a pouting face, a face screaming in fear, an astonished face, a smirking face, and so on. Emoji can be used to express demographic information that can include gender, age, ethnicity, and so on. Emoji 2310 represents a smiling face with an open mouth. Emoji 2312 represents a kissing face. Emoji 2314 represents a flushed face. Emoji 2316 represents a pouting face. Emoji 2320 represents a smiling face. Emoji 2322 represents a smiling face with a stuck-out tongue and winking eye. Emoji 2324 represents a pensive face. Emoji 2326 represents a face screaming in fear.

Figure 23B:
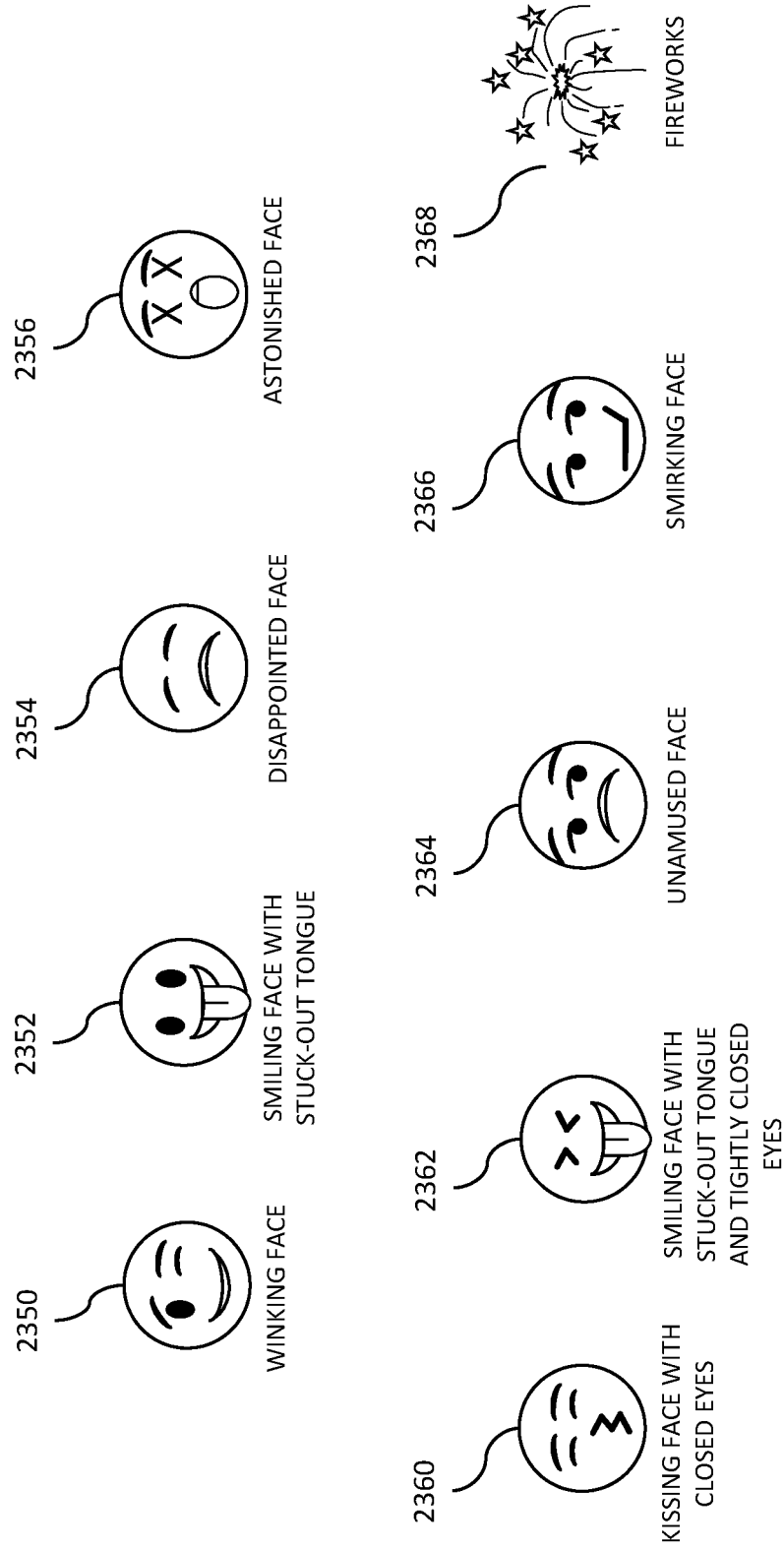
FIG. 23B illustrates additional emoji.

FIG. 23B illustrates additional emoji. The example emoji 2302 illustrate a variety of additional facial expressions. Emoji 2350 represents a winking face. Emoji 2352 represents a smiling face with a stuck-out tongue. Emoji 2354 represents a disappointed face. Emoji 2356 represents an astonished face. Emoji 2360 represents a kissing face with closed eyes. Emoji 2362 represents a smiling face with a stuck-out tongue and tightly closed eyes. Emoji 2364 represents an unamused face. Emoji 2366 represents a smirking face. Emoji 2368 represents fireworks.

Each of the emoji shown in FIG. 23A and FIG. 23B can be included in a database. In embodiments, each emoji can be associated with an index. The database may be a relational database such as a Structured Query Language (SQL) database. One or more tables may be associated with each emoji, and may contain various attributes of the emoji. The attributes may include one or more emotions/mental states associated with the emoji. For example, emoji 2310 and emoji 2320 may be associated with happiness. Some emoji may be associated with multiple emotions. For example, emoji 2364 may be associated with disappointment, worry, and discontent. Additionally, some emoji may not necessarily resemble a human form. For example, emoji 2368 represents fireworks. The fireworks emoji 2368 may be associated with a high level of happiness. Thus, when a high level of happiness is detected, a fireworks emoji 2368 may be presented. This is merely exemplary, and other non-human-form emoji may also be used in disclosed embodiments.

The database may further include attributes, such as one or more action units that are associated with each emoji, as well as action units whose absence can be associated with the emoji. For example, emoji 2350 may be associated with AU46 (wink), AU12 (lip corner puller) and an absence of AU15 (lip corner depressor). The database can also include additional information such as user preferences, and/or user profile information such as gender, age, and/or ethnicity. The user profile and/or user preference information can be used as criteria for determining an emoji to select and/or suggest for insertion into a message and/or post. In some embodiments, more than one emoji may be automatically included in a message. For example, if a user is detected to be very happy, two of emoji 2310 and three of emoji 2368 can be included in the message.

Figure 24:
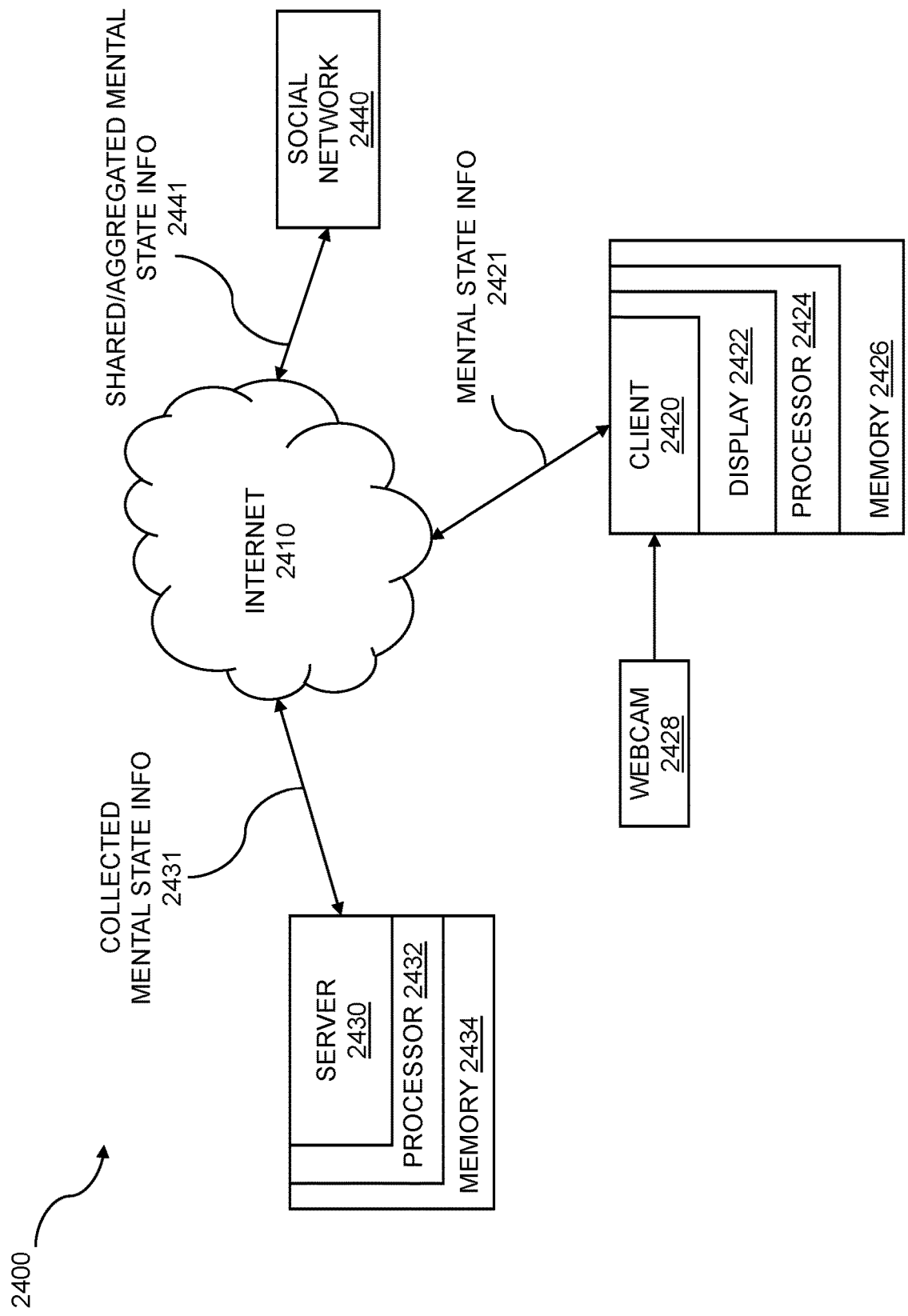
FIG. 24 is a system diagram with sharing across a social network.

FIG. 24 is a system diagram 2400 for sharing across a social network, or a system for sharing mental states. The internet 2410, intranet, or other computer network may be used for communication between the various computers. A client computer 2420 has a memory 2426 for storing instructions and one or more processors 2424 attached to the memory 2426 wherein the one or more processors 2424 can execute instructions. The client computer 2420 may receive image data of various formats from webcam 2428. Webcam 2428 can be physically separate from client computer 2420 or integrated in client computer 2420. An example of the latter is a front-side camera of a smartphone. The client computer 2420 also may have an internet connection to communicate mental state information 2421. The client computer 2420 may also have a display 2422 that may present various renderings to a user. The client computer 2420 may be able to collect mental state data from an individual or a plurality of people as they interact with a rendering. In some embodiments, there may be multiple client computers 2420 that each may collect mental state data from one person or a plurality of people as they interact with a rendering. In other embodiments, the client computer 2420 may receive mental state data collected from a plurality of people as they interact with a rendering. The client computer 2420 may receive an instruction, from the individual, to elect to share the mental state information. Once the mental state data has been collected, the client computer may, if permission is received, upload information to a server 2430, based on the mental state data from the plurality of people who interact with the rendering. The client computer 2420 may communicate with the server 2430 over the internet 2410, some other computer network, or by other method suitable for communication between two computers. In some embodiments, the server 2430 functionality may be embodied in the client computer.

The server 2430 may have an internet connection for receiving mental states or collected mental state information 2431 and have a memory 2434 which stores instructions and one or more processors 2432 attached to the memory 2434 to execute instructions. The server 2430 may receive mental state information collected from a plurality of people as they interact with a rendering from the client computer 2420 or computers, and may analyze the mental state data to produce mental state information. The server 2430 may also aggregate mental state information on the plurality of people who interact with the rendering. The server 2430 may also associate the aggregated mental state information with the rendering and also with the collection of norms for the context being measured. In some embodiments, the server 2430 may also allow user to view and evaluate the mental state information that is associated with the rendering, but in other embodiments, the server 2430 may send the aggregated mental state information 2441 to a social network 2440 to be shared, distributing the mental state information across a computer network. This may be done to share the mental state information across a social network. In some embodiments, the social network 2440 may run on the server 2430. In some embodiments, client computer 2420 and server 2430 may be the same computer.

Each of the above methods may be executed on one or more processors on one or more computer systems. Embodiments may include various forms of distributed computing, client/server computing, and cloud based computing. Further, it will be understood that for each flow chart in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. Each element of the block diagrams and flowchart illustrations, as well as each respective combination of elements in the block diagrams and flowchart illustrations, illustrates a function, step or group of steps of the methods, apparatus, systems, computer program products, and/or computer-implemented methods. Any and all such functions may be implemented by computer program instructions, by special-purpose hardware-based computer systems, by combinations of special purpose hardware and computer instructions, by combinations of general purpose hardware and computer instructions, and so on. Any and all of which may be generally referred to herein as a "circuit," "module," or "system."

A programmable apparatus which executes any of the above-mentioned computer program products or computer implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM, Flash, MRAM, FeRAM, or phase change memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for data sharing comprising:
   collecting mental state data of an individual, wherein the mental state data includes facial image data of the individual;
   analyzing the mental state data using a neural network to produce mental state information and a plurality of emotional intensity metrics, wherein the neural network was trained to identify facial expressions and mental states;
   sharing the mental state information across a social networking platform;
   coalescing the plurality of emotional intensity metrics into a summary intensity metric;
   inferring mental states based on both the mental state data which was collected and the summary intensity metric;
   identifying a user on the social networking platform who is associated with at least one mental state similar to at least one of the inferred mental states, wherein the identifying a user on the social networking platform includes searching a group specifically created to share mental state information; and
   providing an identification of the user to the individual as having a similar mental state to at least one of the inferred mental states.

2. The method of claim 1 further comprising electing, by the individual, to share the mental state information.

3. The method according to claim 2 further comprising presenting the mental state information to the individual, prior to the electing.

4. The method of claim 1 wherein the mental state data is collected over a period of time and the mental state information that is shared is a reflection of a mood for the individual.

5. The method of claim 4 wherein the mood includes one of a group comprising frustration, confusion, disappointment, hesitation, cognitive overload, focusing, being engaged, attending, boredom, exploration, confidence, trust, delight, and satisfaction.

6. The method of claim 1 wherein the sharing includes posting mental state information to a social networking platform web page.

7. The method of claim 1 further comprising uploading the mental state information to a server.

8. The method of claim 1 further comprising distributing the mental state information across a computer network.

9. The method of claim 1 wherein the mental state data includes one of a group comprising physiological data, facial data, or actigraphy data.

10. The method of claim 9 wherein a webcam is used to capture one or more of the facial data or the physiological data.

11. The method of claim 9 wherein the physiological data includes one or more of electrodermal activity, heart rate, heart rate variability, skin temperature, and respiration.

12. The method according to claim 1 further comprising communicating an image of the individual with the mental state information that is being shared.

13. The method according to claim 12 wherein the image of the individual is from a peak time of mental state activity.

14. The method of claim 1 further comprising restricting distribution of the mental state information to a subset of the social networking platform.

15. The method of claim 1 further comprising sharing aggregated mental state information across the social networking platform.

16. The method according to claim 1 wherein the mental state data is collected as the individual interacts with a web-enabled application.

17. The method according to claim 16 further comprising forwarding a reference to the web-enabled application as a part of the sharing of the mental state information.

18. The method of claim 17 wherein the forwarding includes a video of material from the web-enabled application.

19. The method according to claim 16 wherein the sharing is part of a rating system for the web-enabled application.

20. The method of claim 1 further comprising translating the mental state information into a representative icon for sharing across the social networking platform.

21. The method of claim 1 wherein the collecting mental state data of an individual includes collecting audio data.

22. The method of claim 21 wherein the analyzing the mental state data of the individual includes analyzing the audio data that was collected.

23. A computer program product embodied in a non-transitory computer readable medium for data sharing, the computer program product comprising code which causes one or more processors to perform operations of:
   collecting mental state data of an individual, wherein the mental state data includes facial image data of the individual;
   analyzing the mental state data of the individual using a neural network to produce mental state information and a plurality of emotional intensity metrics, wherein the neural network was trained to identify facial expressions and mental states;
   sharing the mental state information across a social networking platform;
   coalescing the plurality of emotional intensity metrics into a summary intensity metric;
   inferring mental states based on both the mental state data which was collected and the summary intensity metric;
   identifying a user on the social networking platform who is associated with at least one mental state similar to at least one of the inferred mental states, wherein the identifying a user on the social networking platform includes searching a group specifically created to share mental state information; and providing an identification of the user to the individual as having a similar mental state to at least one of the inferred mental states.

24. A system for data sharing:

a memory for storing instructions;

one or more processors attached to the memory wherein the one or more processors are configured to:

collect mental state data of an individual, wherein the mental state data includes facial image data of the individual;

analyze the mental state data of the individual using a neural network to produce mental state information and a plurality of emotional intensity metrics, wherein the neural network was trained to identify facial expressions and mental states;

share the mental state information across a social networking platform;

coalesce the plurality of emotional intensity metrics into a summary intensity metric;

infer mental states based on both the mental state data which was collected and the summary intensity metric;

identify a user on the social networking platform who is associated with at least one mental state similar to at least one of the inferred mental states, wherein identifying a user on the social networking platform includes searching a group specifically created to share mental state information; and provide an identification of the user to the individual as having a similar mental state to at least one of the inferred mental states.

25. The method of claim 1 wherein the neural network comprises a multilayered analysis engine used for emotional analysis.

26. The method of claim 1 wherein the neural network is a convolutional neural network.

27. The method of claim 1 wherein the neural network provides an output to a pooling layer.

28. The method of claim 1 wherein the identifying a user on the social networking platform includes searching a contact list for the individual.

29. The method of claim 28 wherein the identifying a user on the social networking platform includes searching an extended contact list for the individual, wherein the extended contact list includes contact lists for users in the contact list for the individual.

* * * * *